(12) United States Patent
Yazaki et al.

(10) Patent No.: US 11,564,665 B2
(45) Date of Patent: Jan. 31, 2023

(54) ULTRASONIC PROBE, ULTRASONIC DIAGNOSTIC DEVICE, AND MANUFACTURING METHOD OF ULTRASONIC PROBE

(71) Applicant: Hitachi, Ltd., Tokyo (JP)

(72) Inventors: Toru Yazaki, Tokyo (JP); Yutaka Igarashi, Tokyo (JP); Yoshihiro Hayashi, Tokyo (JP); Tsuneo Kawamata, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 465 days.

(21) Appl. No.: 16/801,355

(22) Filed: Feb. 26, 2020

(65) Prior Publication Data

US 2020/0300817 A1    Sep. 24, 2020

(30) Foreign Application Priority Data

Mar. 22, 2019    (JP) .............................. JP2019-054886

(51) Int. Cl.
*G01N 29/24* (2006.01)
*G01N 29/34* (2006.01)
(Continued)

(52) U.S. Cl.
CPC ............... *A61B 8/58* (2013.01); *A61B 8/585* (2013.01); *G01H 3/005* (2013.01); *G01N 29/24* (2013.01);
(Continued)

(58) Field of Classification Search
CPC .. G01N 29/34; G01N 29/24; G01N 2291/106; G01N 29/341; A61B 8/585; A61B 8/58; H01L 41/042; G01H 3/005
(Continued)

(56) References Cited

U.S. PATENT DOCUMENTS

| 5,027,821 A | * | 7/1991 | Hirama | ................. G01S 7/5205 |
| | | | | 600/447 |
| 6,225,729 B1 | * | 5/2001 | Izumi | ..................... G10K 11/02 |
| | | | | 310/334 |

(Continued)

FOREIGN PATENT DOCUMENTS

| JP | 2002-159492 A | 6/2002 |
| JP | 2004-174227 A | 6/2004 |

(Continued)

OTHER PUBLICATIONS

Japanese-language Office Action issued in Japanese Application No. 2019-054886 dated Mar. 15, 2022 with English translation (eight (8) pages).

*Primary Examiner* — Jacques M Saint Surin
(74) *Attorney, Agent, or Firm* — Crowell & Moring LLP

(57) ABSTRACT

An object of the invention is to provide an ultrasonic probe, an ultrasonic diagnostic device, and a manufacturing method of the ultrasonic probe, which are capable of reducing a product defect rate. An ultrasonic probe according to one embodiment includes a plurality of channels. Each of the plurality of channels includes a vibrator that outputs an ultrasonic wave, and a transmission circuit unit that changes an output in response to an input transmission signal and causes the vibrator to output the ultrasonic wave by driving the vibrator with the output. Here, the transmission circuit unit includes a stop signal holding circuit that holds a stop signal when the stop signal is input in advance, and selects whether to change the output in response to the transmission signal based on whether the stop signal is held.

4 Claims, 21 Drawing Sheets

(51) Int. Cl.
  *H01L 41/04* (2006.01)
  *G01H 3/00* (2006.01)
  *A61B 8/00* (2006.01)

(52) U.S. Cl.
  CPC .......... *G01N 29/34* (2013.01); *H01L 41/042* (2013.01); *G01N 2291/106* (2013.01)

(58) Field of Classification Search
  USPC ........................................................ 600/459
  See application file for complete search history.

(56) References Cited

U.S. PATENT DOCUMENTS

| | | | |
|---|---|---|---|
| 7,766,838 B2 * | 8/2010 | Yagi | G01N 29/225 |
| | | | 600/459 |
| 8,727,994 B2 * | 5/2014 | Kim | A61B 8/4483 |
| | | | 310/309 |
| 9,089,874 B2 * | 7/2015 | Asafusa | B06B 1/0292 |
| 10,390,794 B2 * | 8/2019 | Kuroiwa | A61B 8/4438 |
| 2004/0220463 A1 | 11/2004 | Satoh | |
| 2006/0145059 A1 | 7/2006 | Lee et al. | |
| 2008/0225639 A1 | 9/2008 | Hongou | |
| 2015/0157299 A1 | 6/2015 | Hopple et al. | |
| 2017/0176581 A1 | 6/2017 | Ku | |

FOREIGN PATENT DOCUMENTS

| | | |
|---|---|---|
| JP | 2004-229979 A | 8/2004 |
| JP | 2006-343315 A | 12/2006 |
| JP | 2008-220753 A | 9/2008 |
| JP | 2009-261611 A | 11/2009 |
| JP | 2018-68363 A | 5/2018 |

* cited by examiner

[FIG. 1]
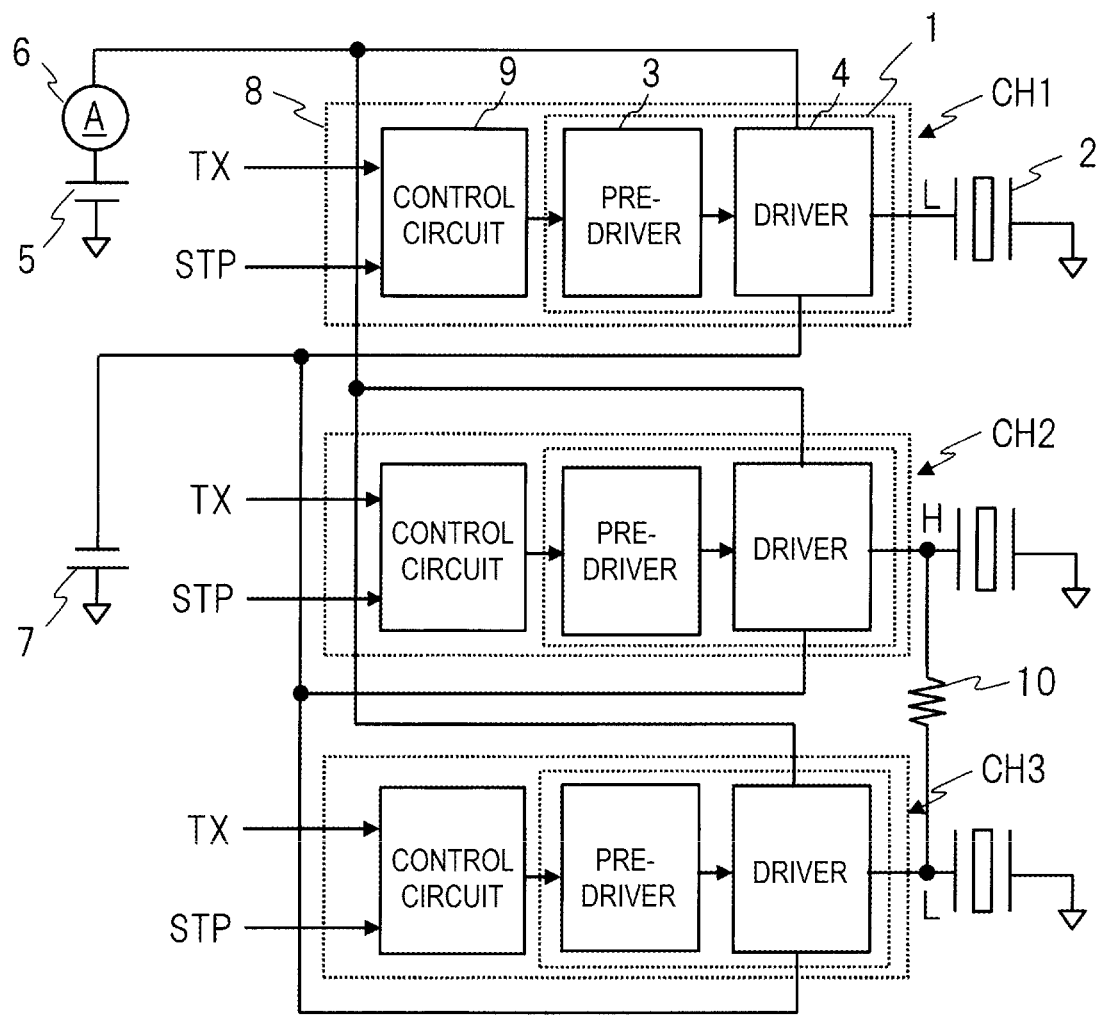
2: VIBRATOR
8: TRANSMISSION CIRCUIT UNIT
CH: CHANNEL
STP: STOP SIGNAL
TX: TRANSMISSION SIGNAL

[FIG. 2]
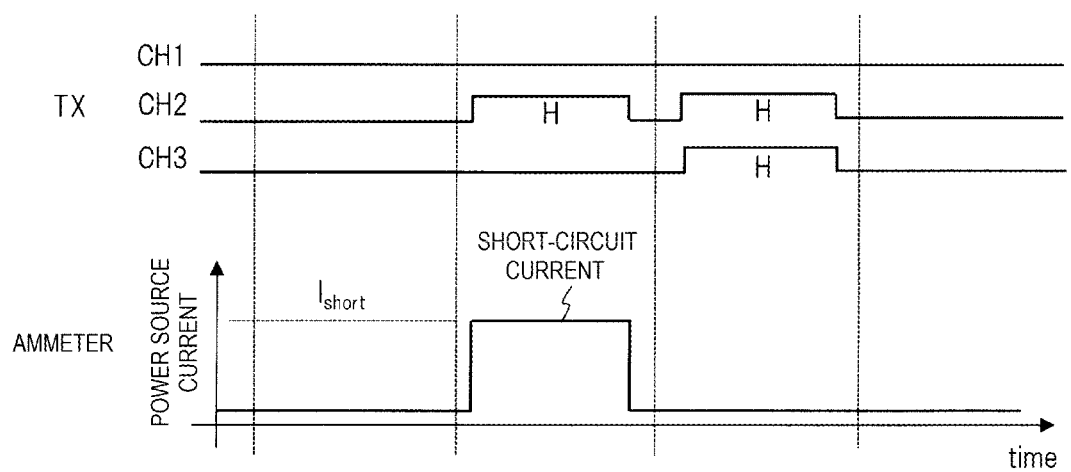

[FIG. 4]
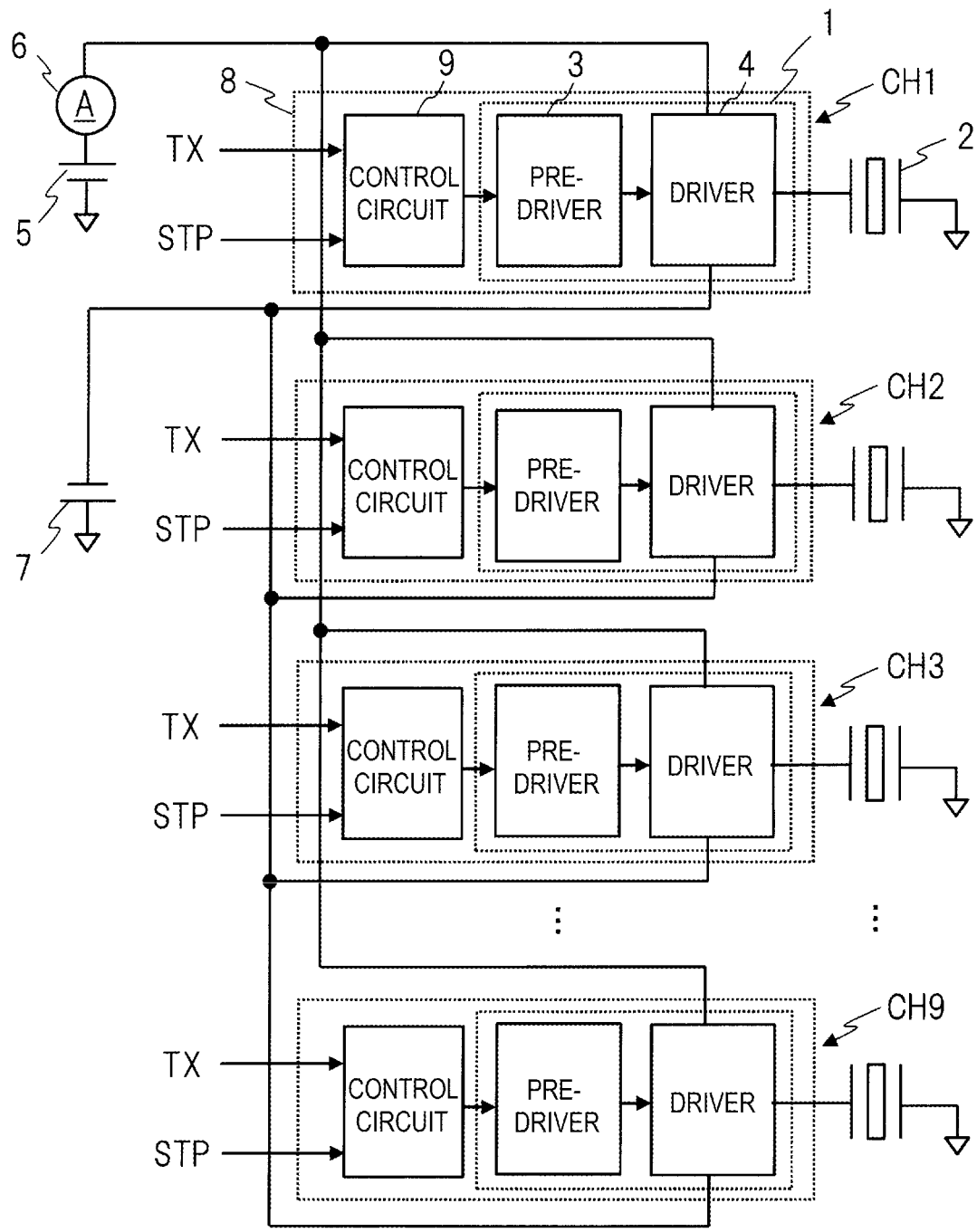

[FIG. 5]
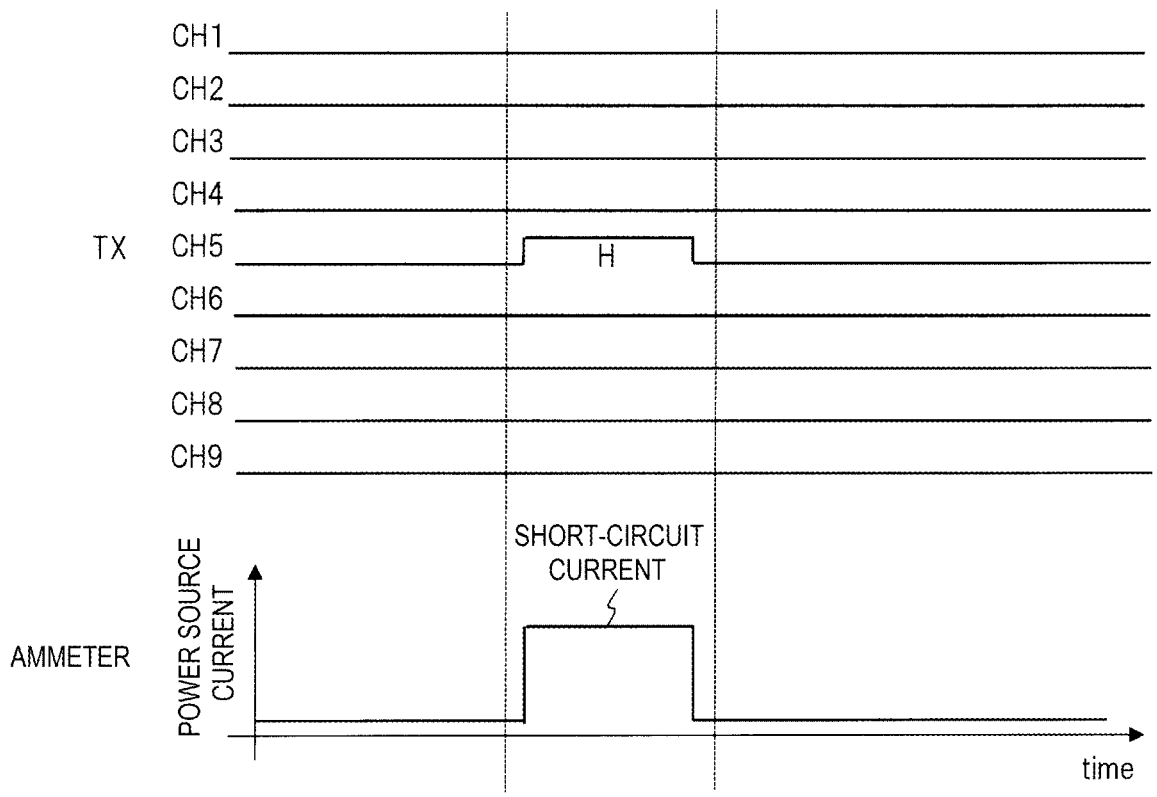

[FIG. 6]
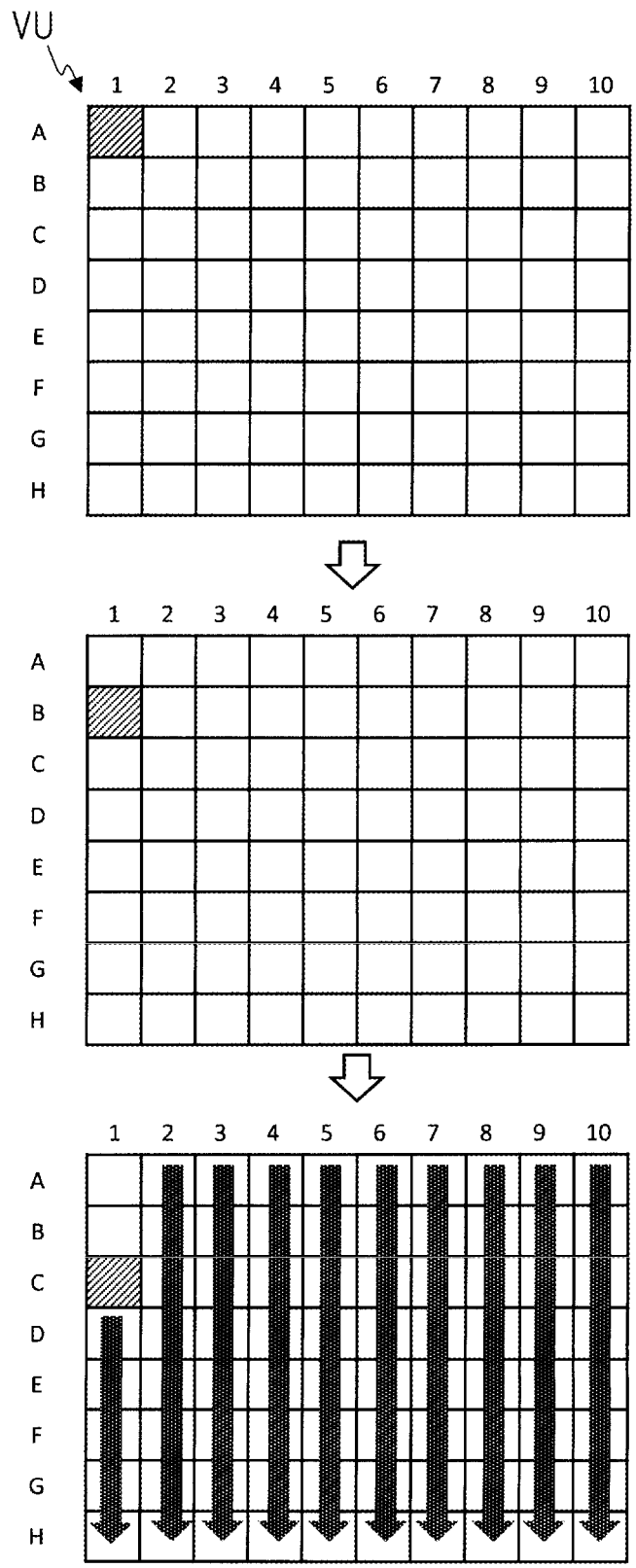

[FIG. 7]
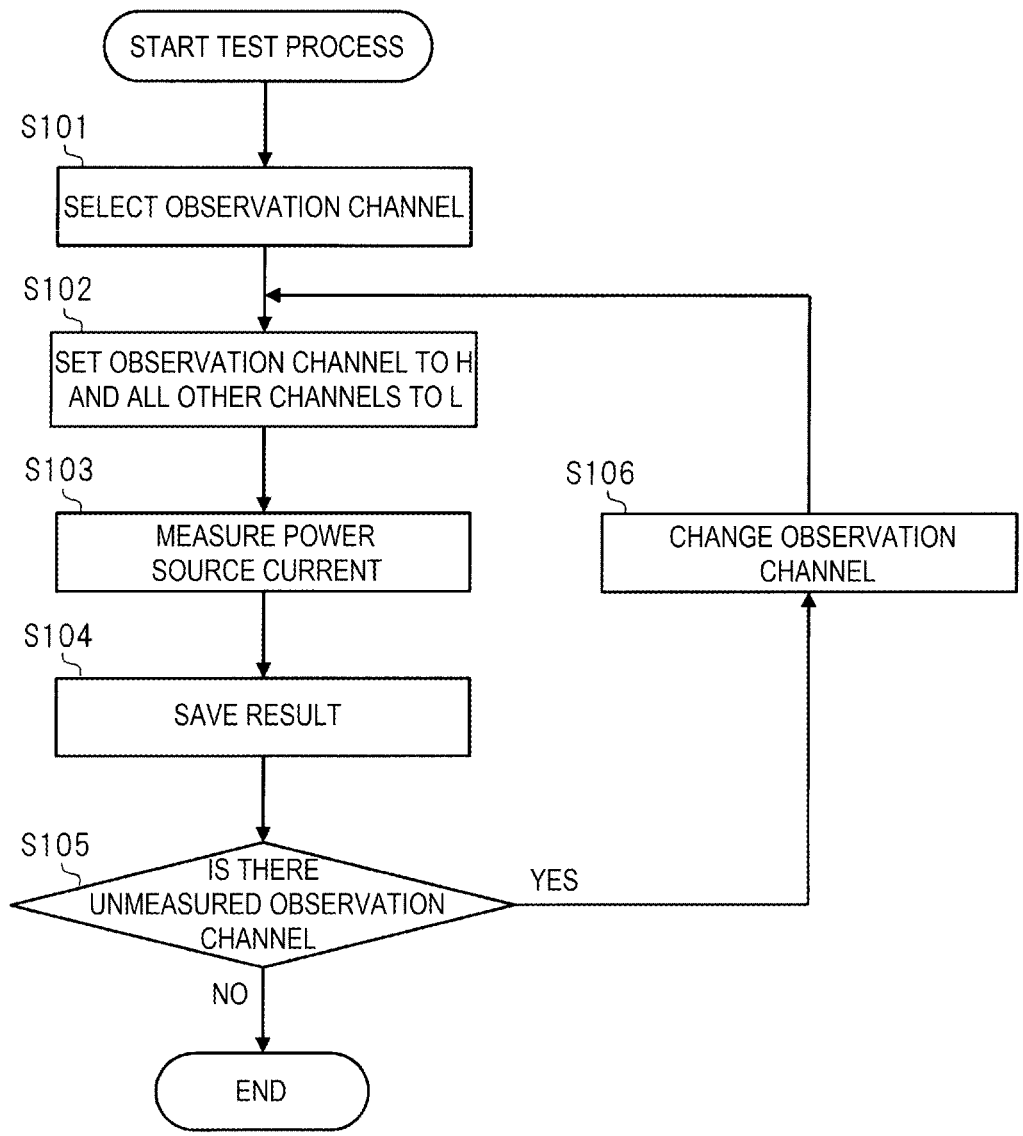

[FIG. 8]
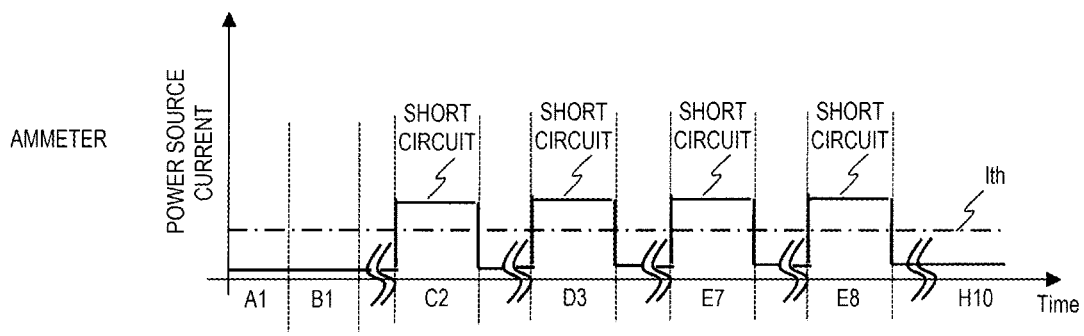
[FIG. 9]
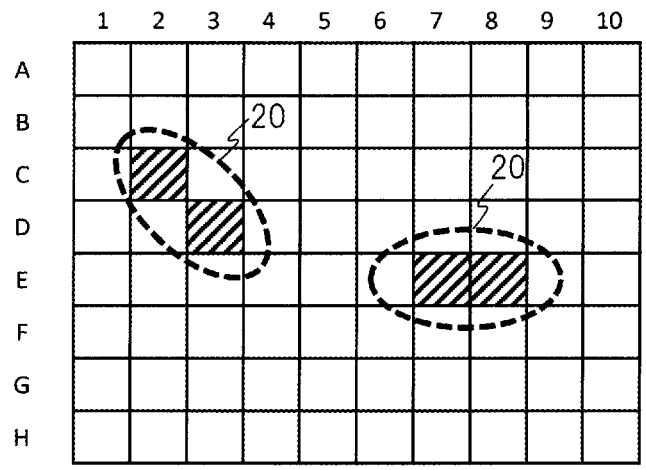

[FIG. 10]
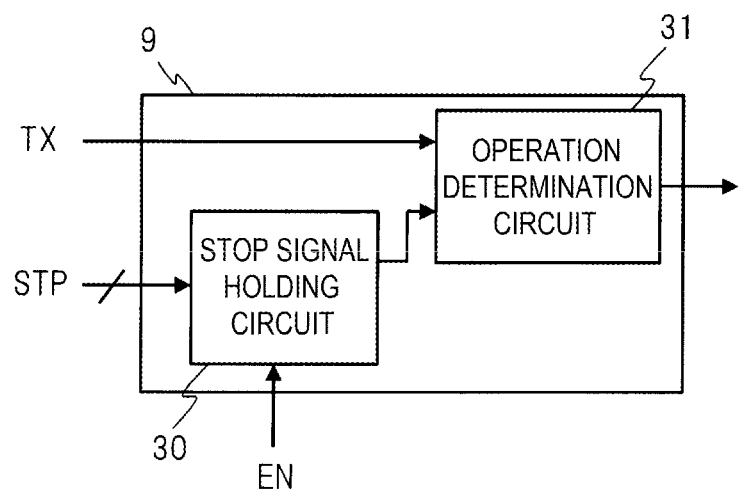
[FIG. 11]
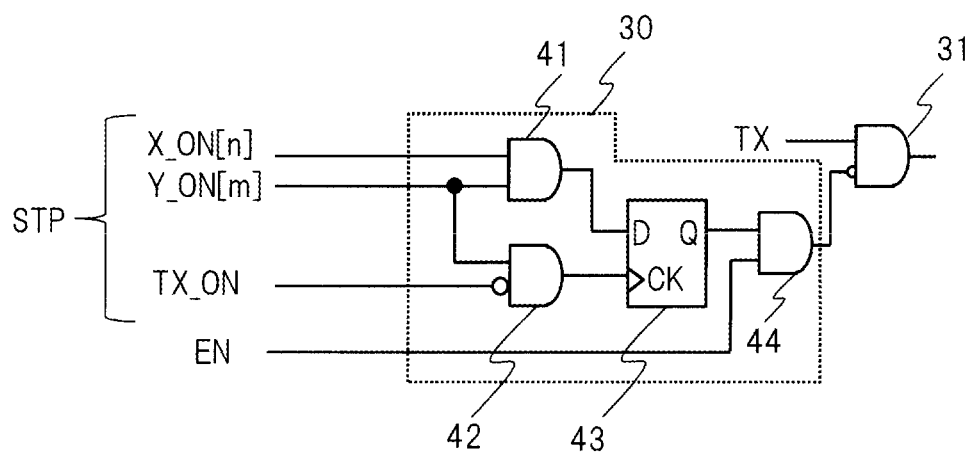

[FIG. 12]
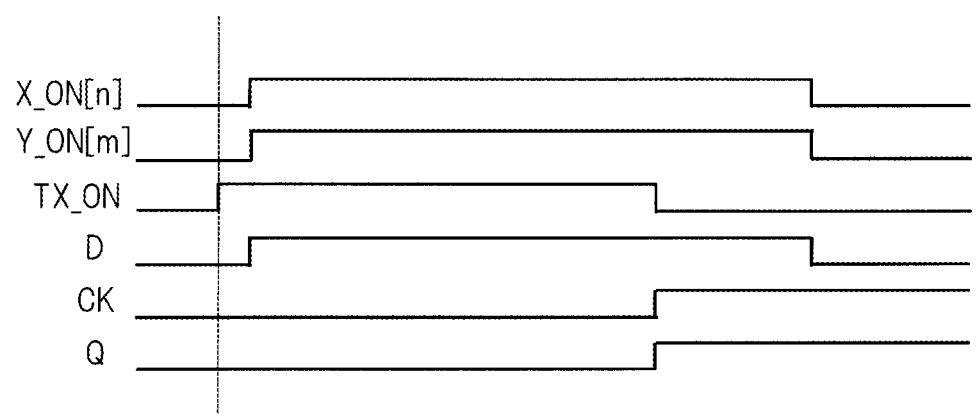

[FIG. 13]
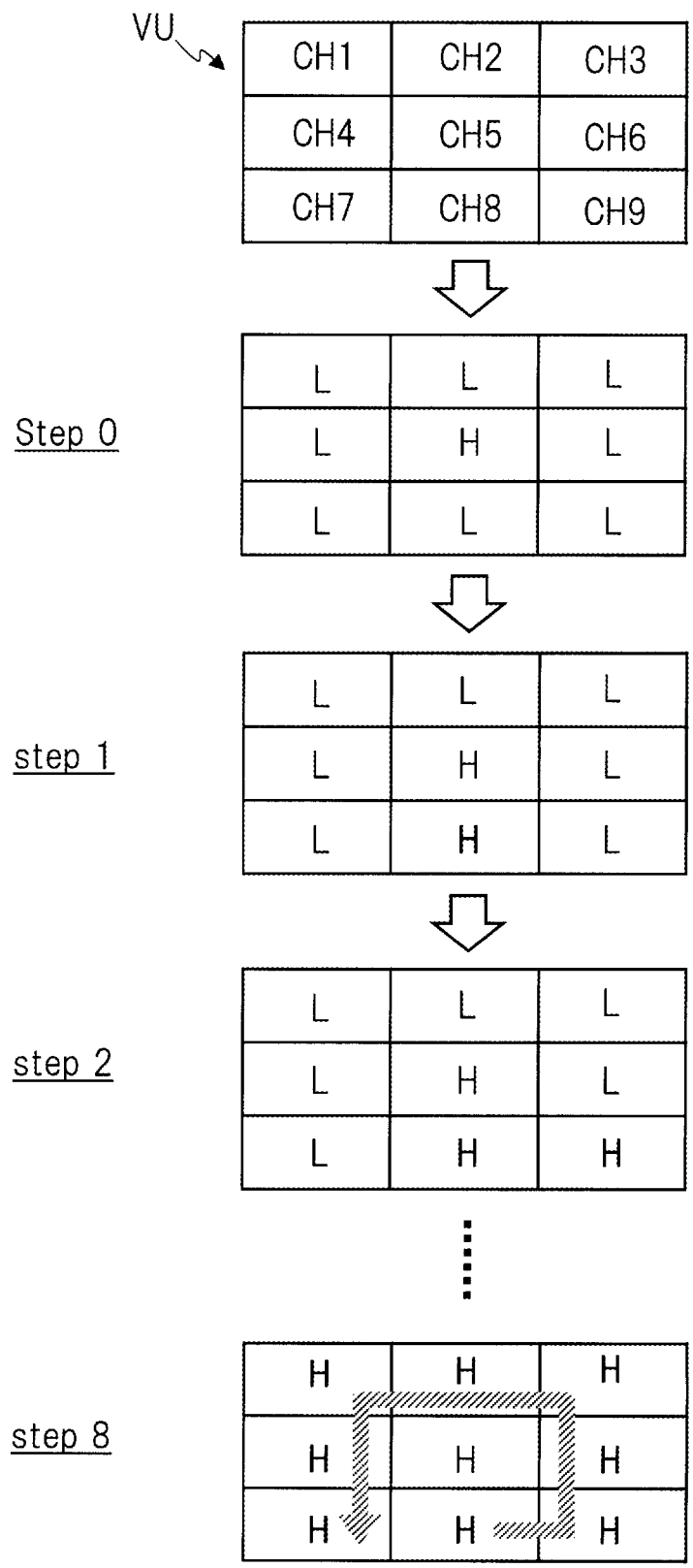

[FIG. 14]
CASE 1
· CH5-CH9 IS
SHORT-CIRCUITED
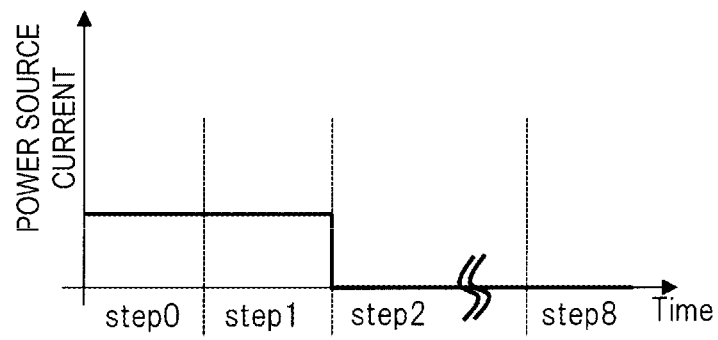
CASE 2
· CH5-CH7 IS
SHORT-CIRCUITED
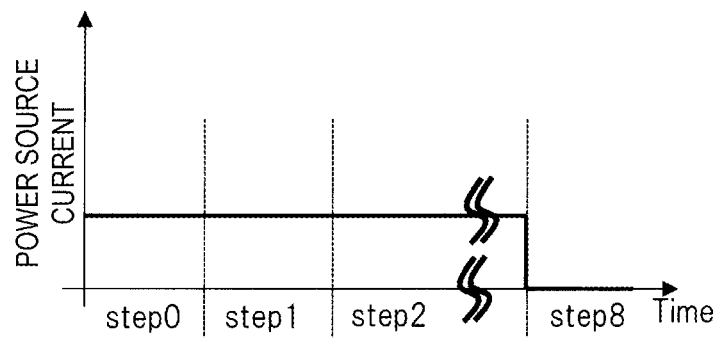
CASE 3
· CH5-CH7 IS
SHORT-CIRCUITED
· CH5-CH9 IS
SHORT-CIRCUITED
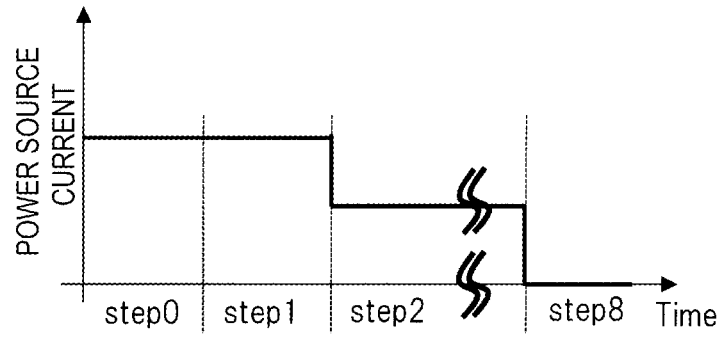

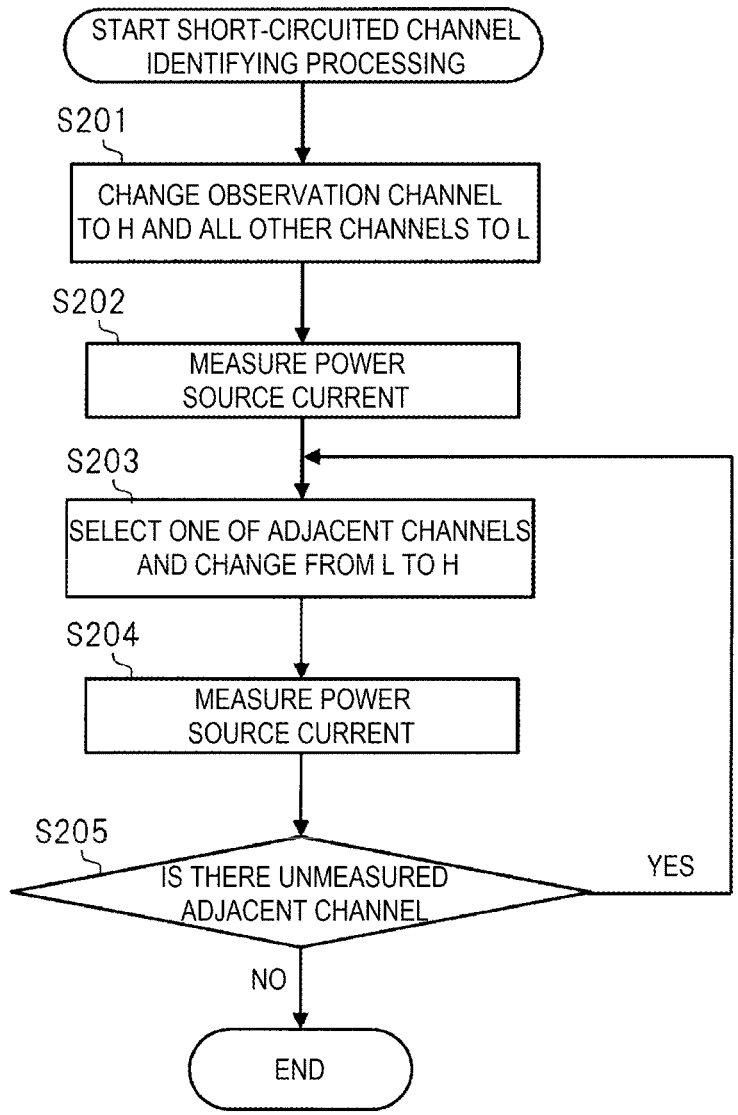
[FIG. 15]

[FIG. 16]
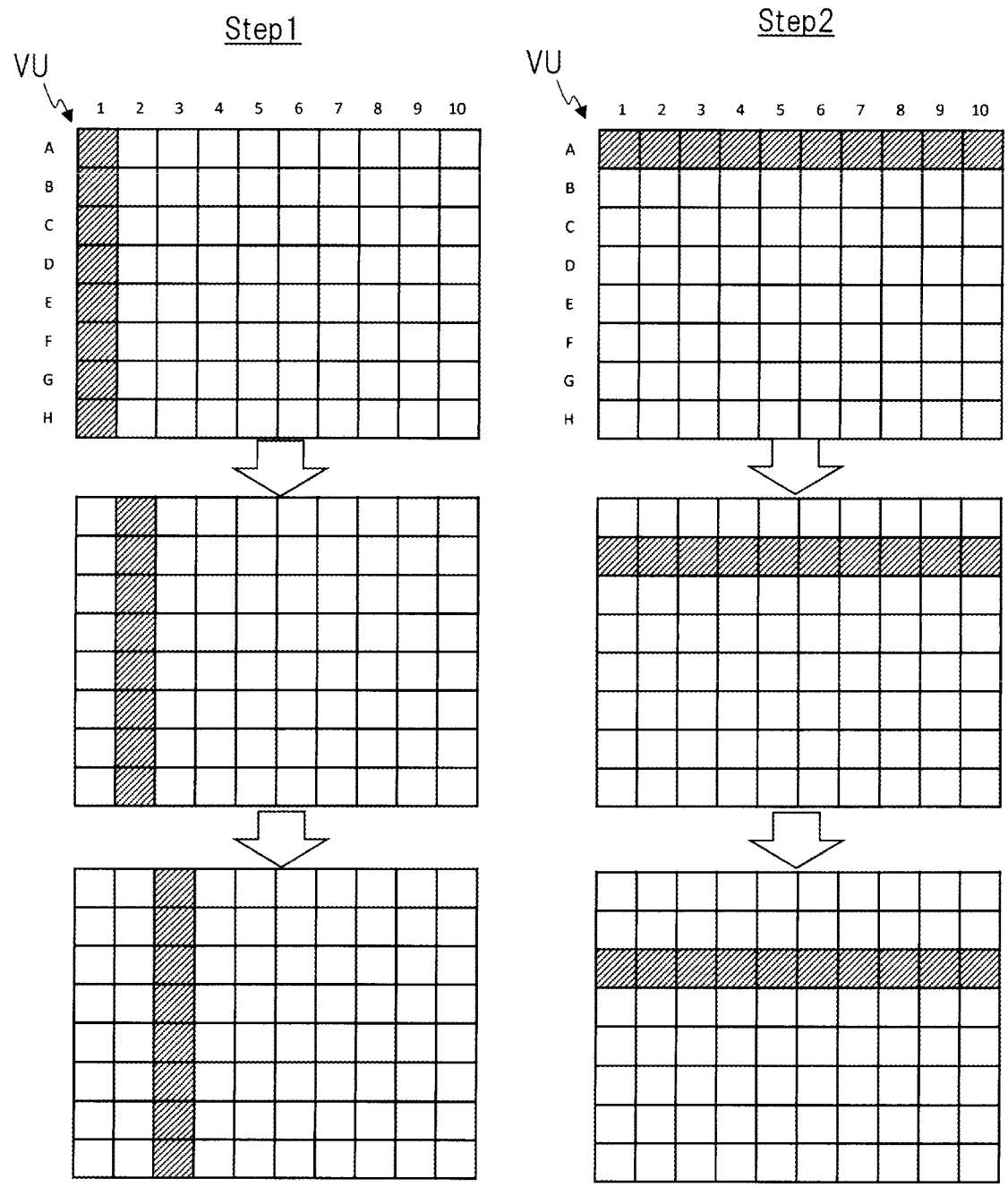

[FIG. 17]
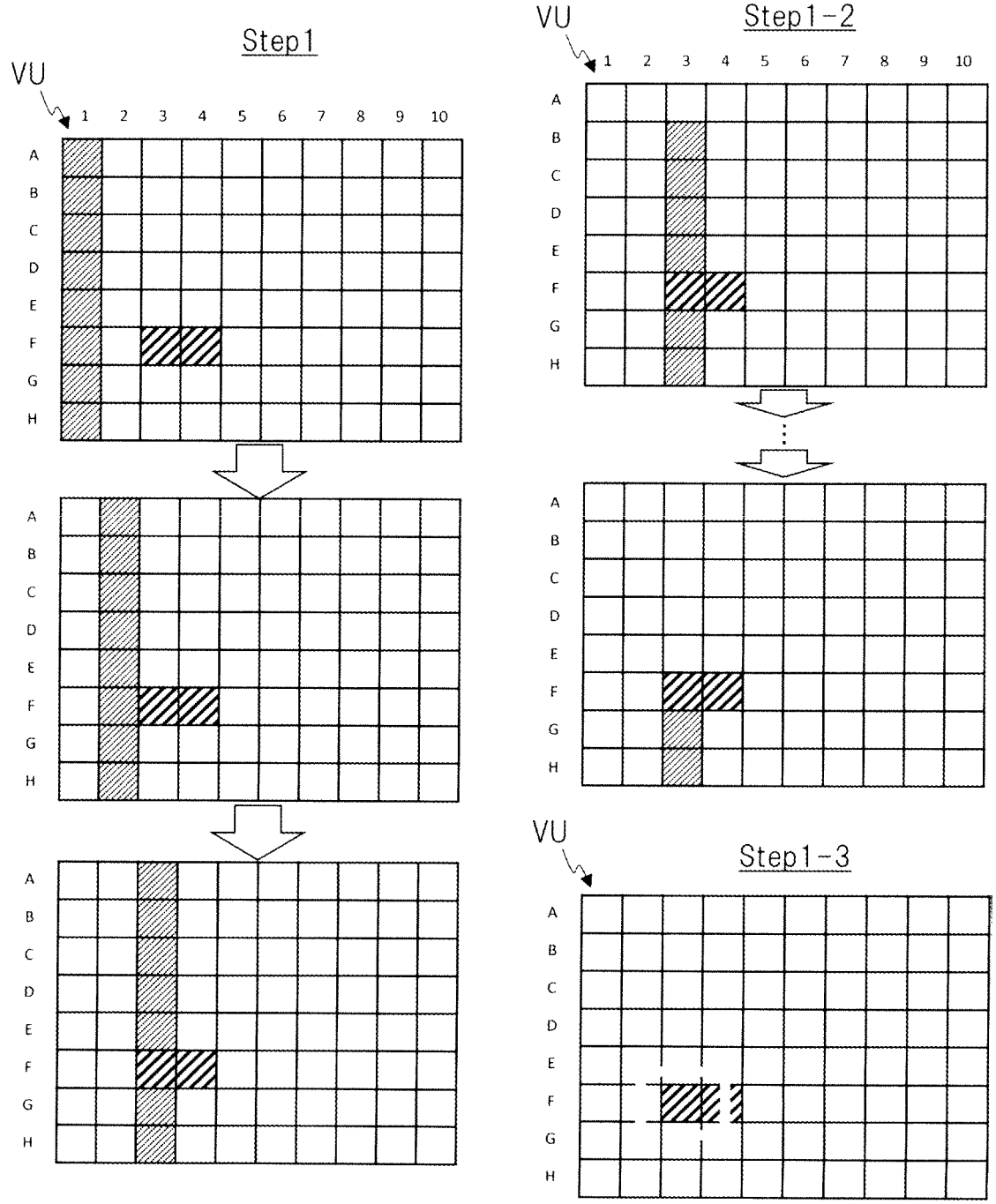

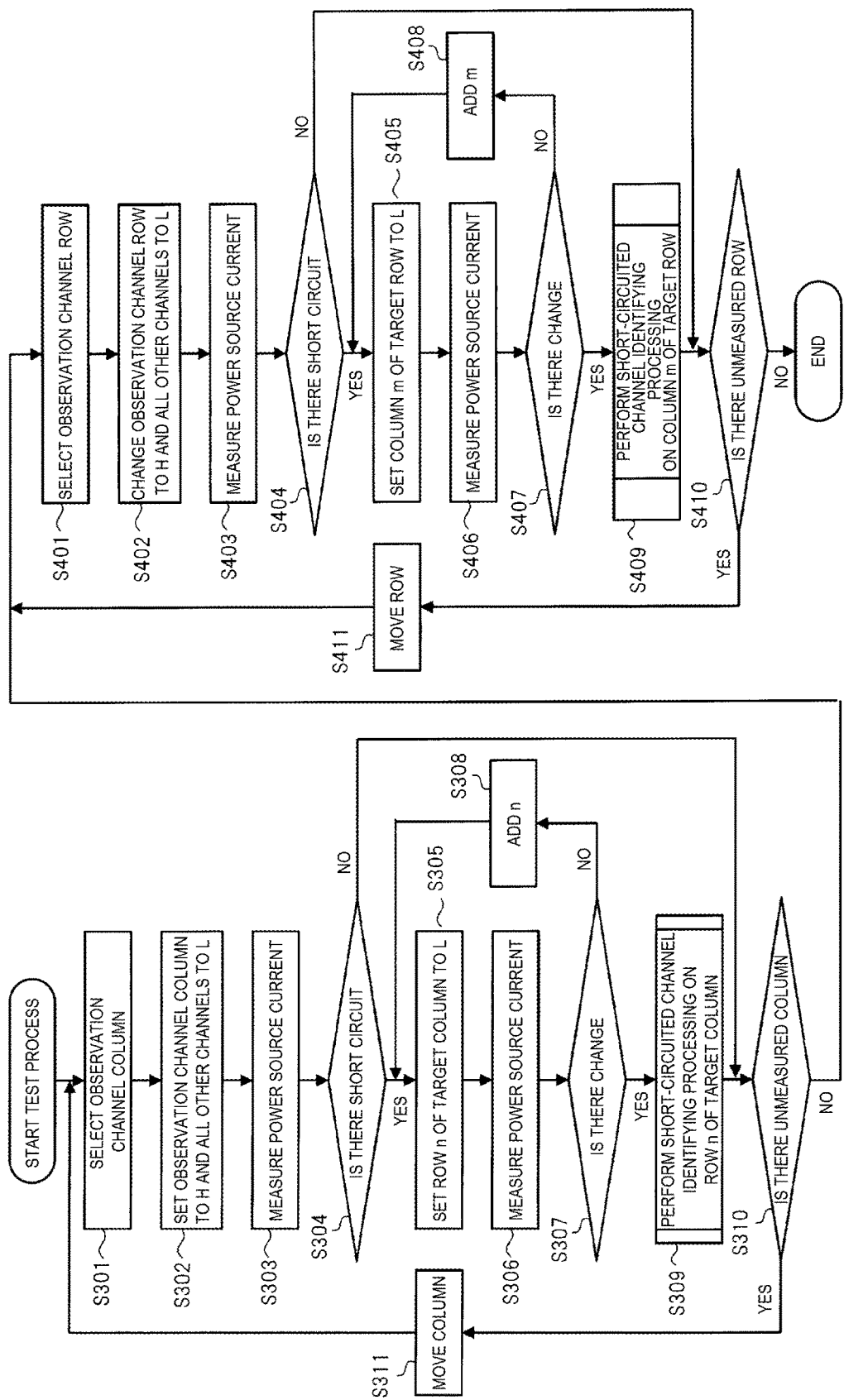
[FIG. 18]

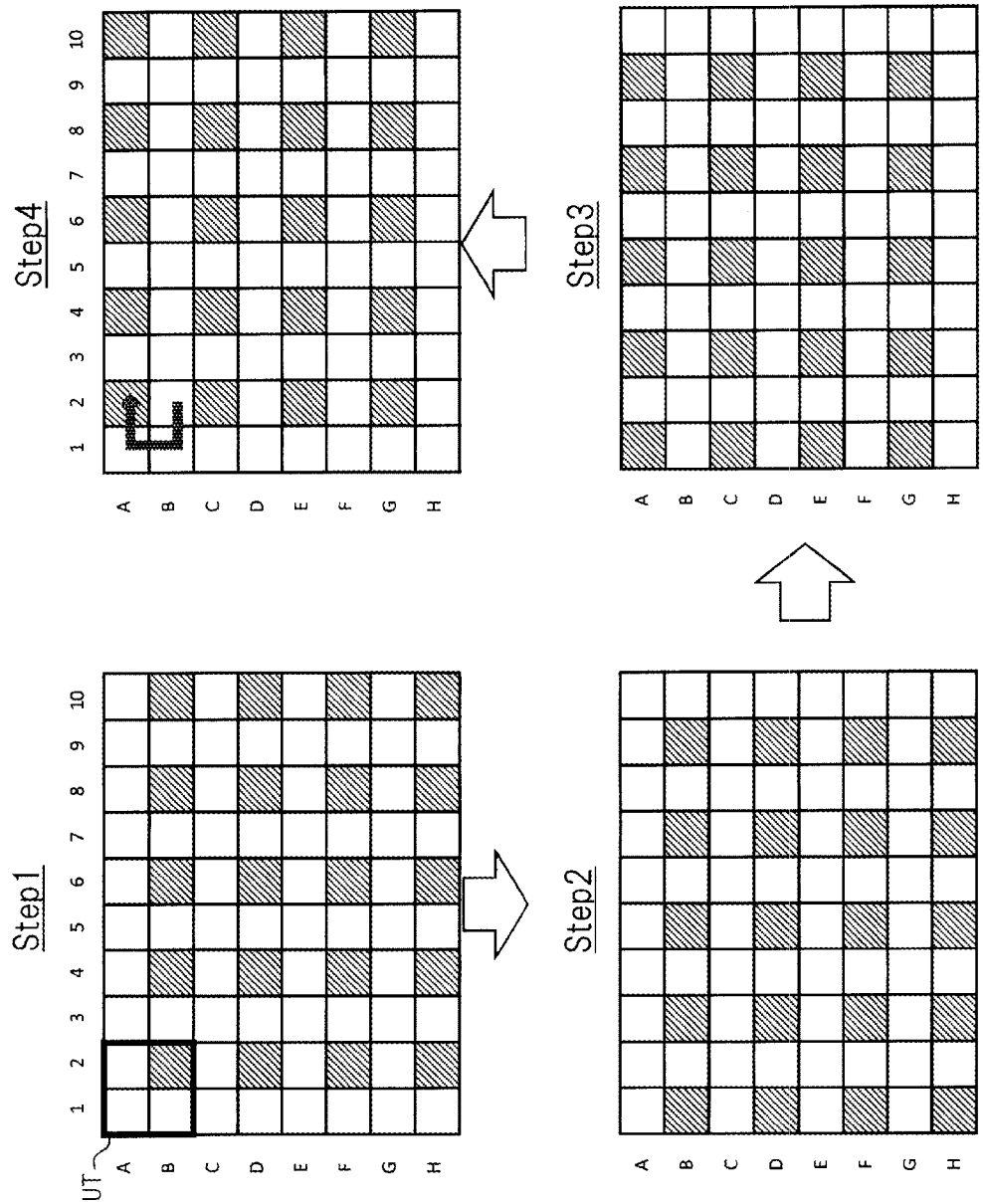
[FIG. 19]

[FIG. 20]
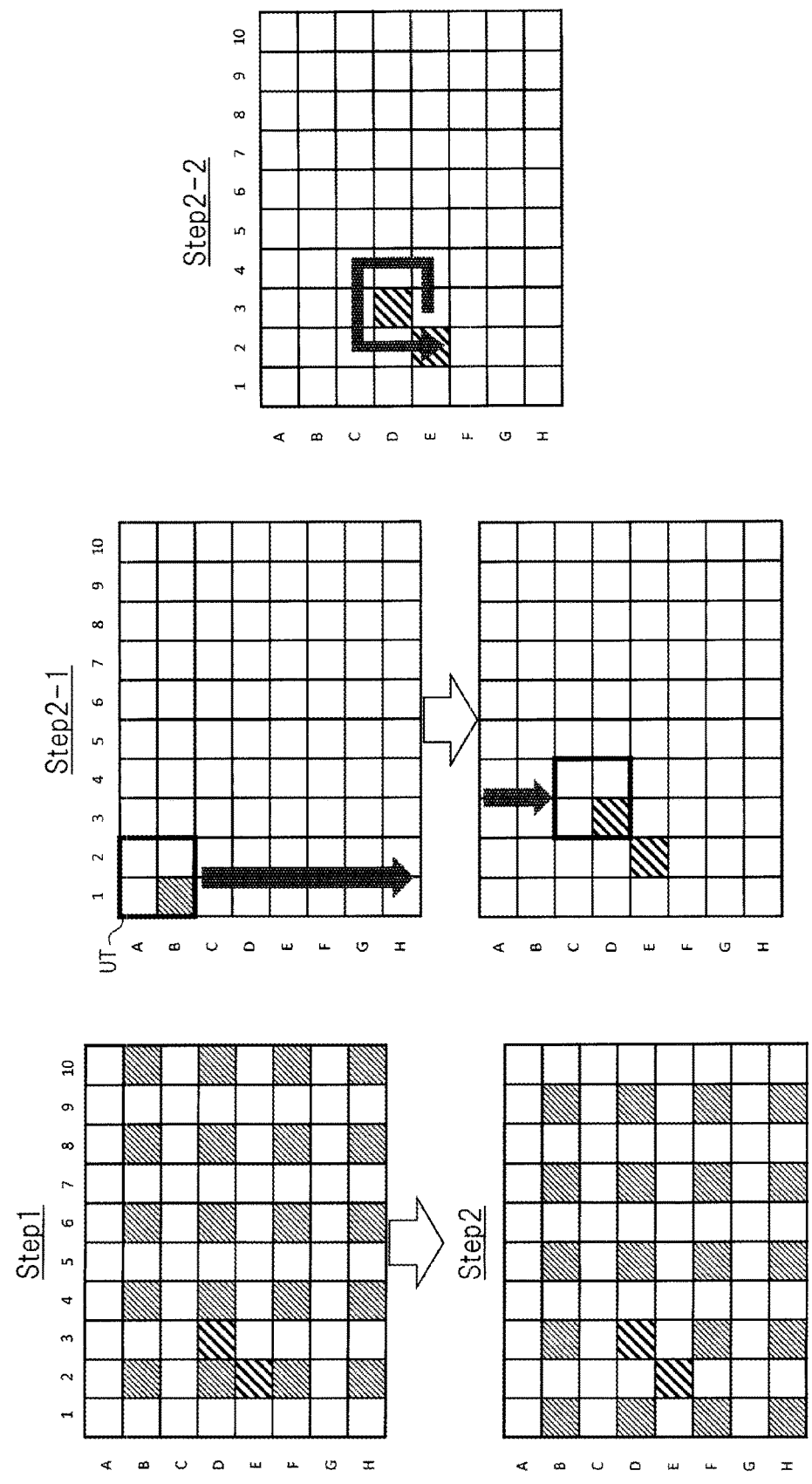

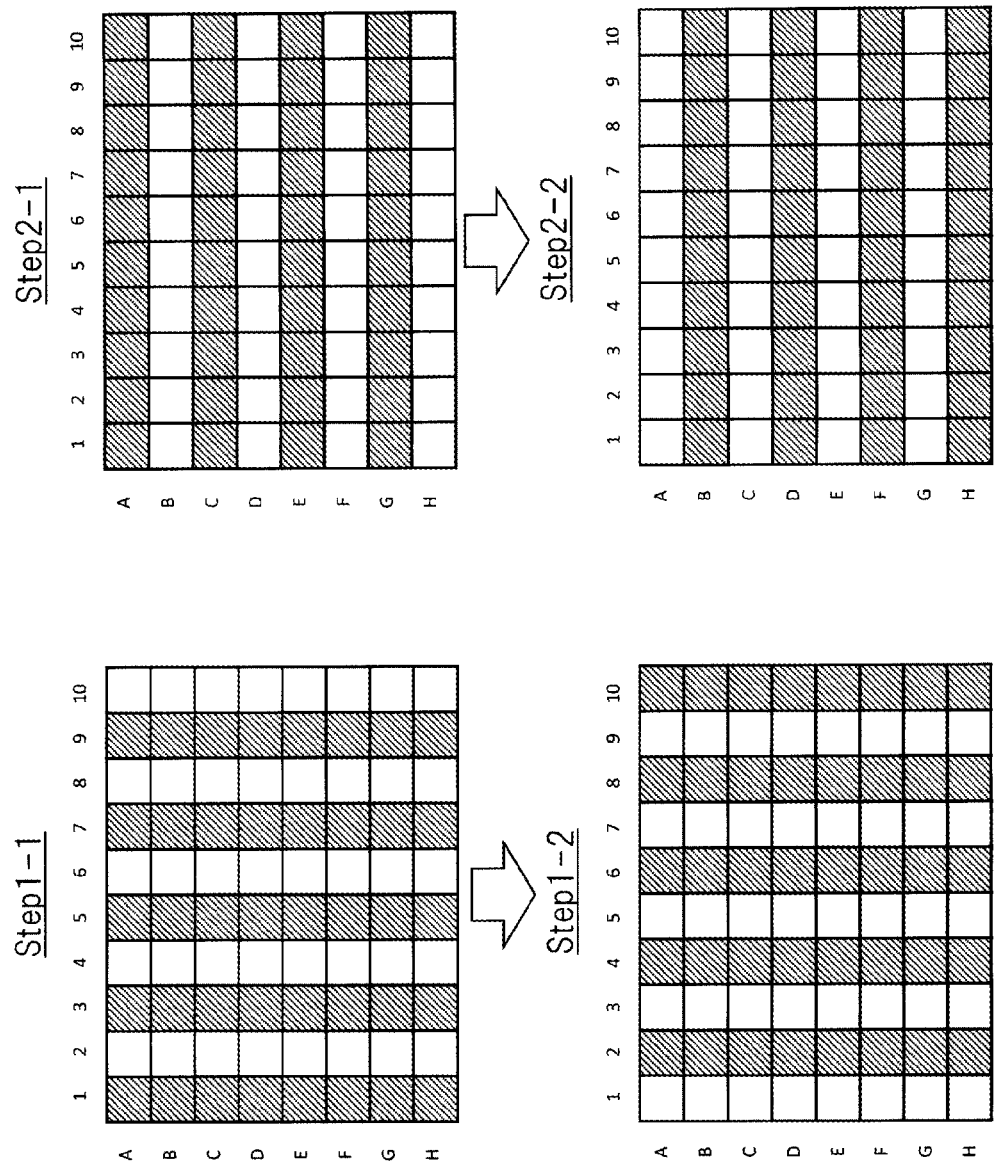
[FIG. 21]

[FIG. 22]
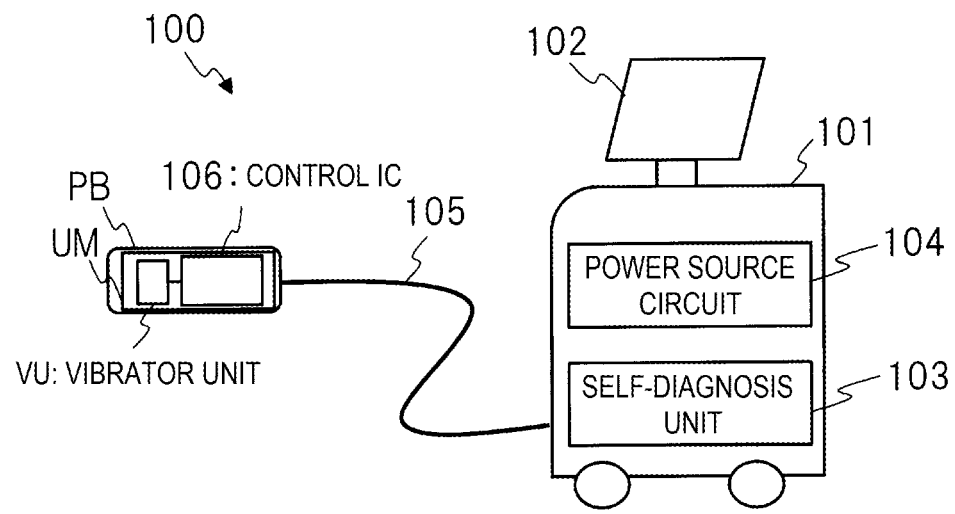
[FIG. 23]
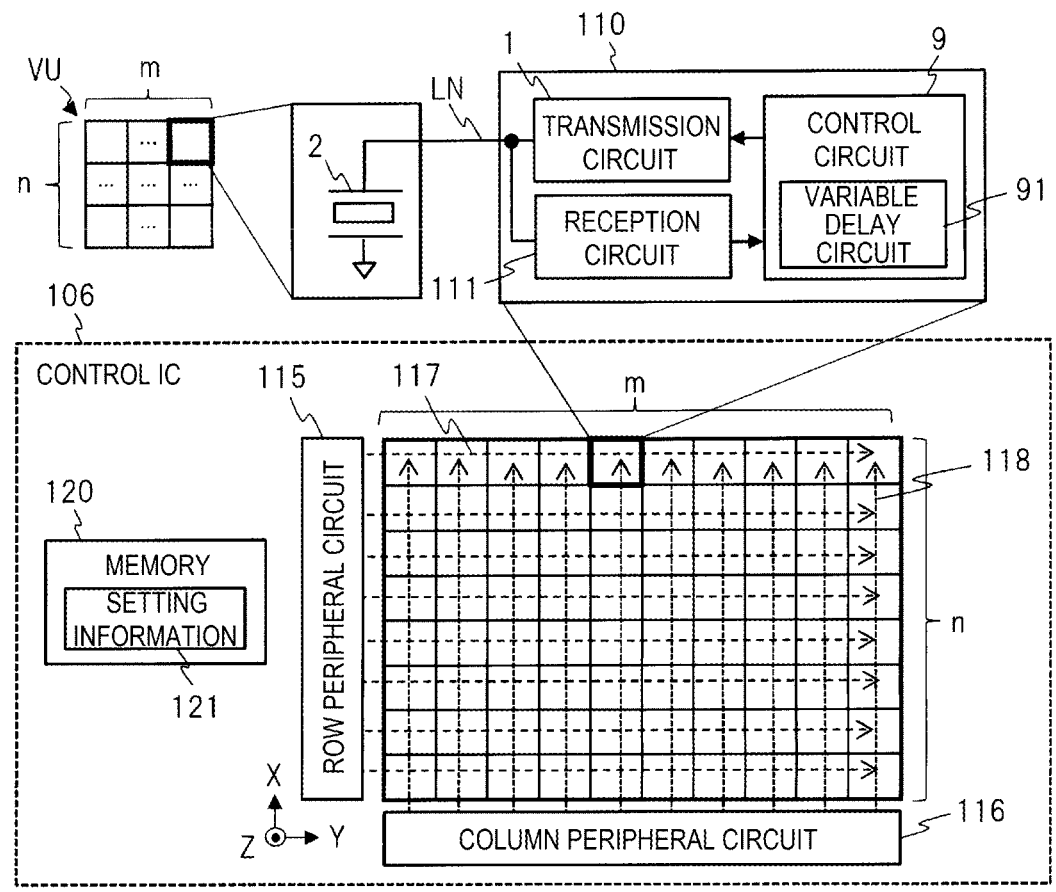

[FIG. 24]
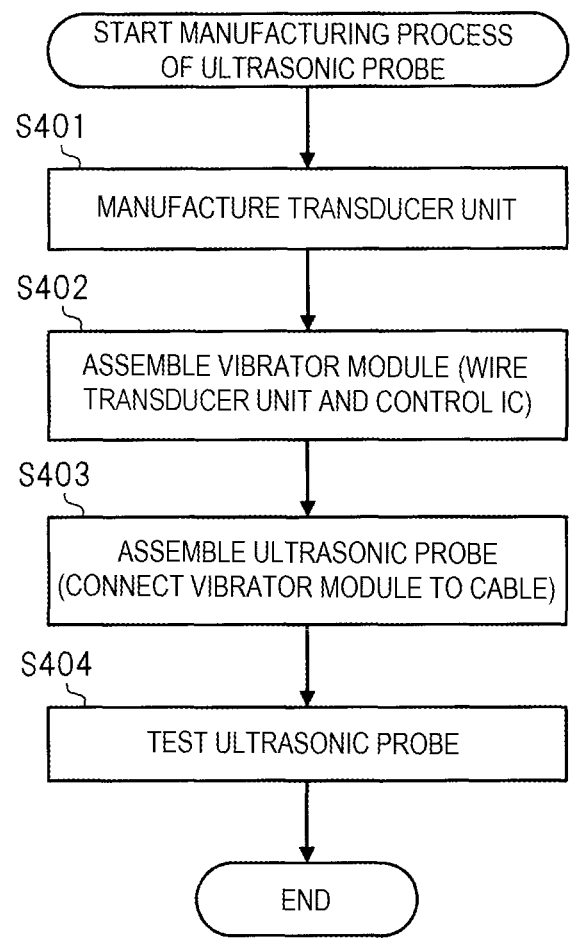

ULTRASONIC PROBE, ULTRASONIC DIAGNOSTIC DEVICE, AND MANUFACTURING METHOD OF ULTRASONIC PROBE

TECHNICAL FIELD

The present invention relates to an ultrasonic probe, an ultrasonic diagnostic device, and a manufacturing method of the ultrasonic probe, and particularly relates to a matrix probe.

BACKGROUND ART

PTL 1 discloses an ultrasonic probe in which a vibrator, a pulser that supplies a pulse signal to the vibrator, and a signal reception unit that receives an ultrasonic echo via the vibrator are provided for each channel, and a test control unit is provided. The test control unit generates a sine wave that is a test signal, and transmits the test signal to the signal reception unit via an FET in the pulser. By causing a device body to perform image processing based on the test signal received by the signal reception unit, it is possible to test a transmission path of the test signal.

PRIOR ART LITERATURE

Patent Literature

PTL 1: JP-A-2008-220753

SUMMARY OF INVENTION

Technical Problem

An ultrasonic probe (1 Dimension (D) probe) in the related art controls a transmission direction of a transmission ultrasonic signal by giving a delay to a transmission signal applied to each of vibrators arranged side by side in a strip shape. Similarly, the 1D probe can acquire an ultrasonic image by giving a delay to each reception signal from a target and adding up the reception signals. However, the 1D probe can only control a direction of a target of transmission and reception in one dimension.

In recent years, attention has been paid to a technology of an ultrasonic probe called a matrix probe (2D probe) in which vibrators arranged two-dimensionally and micro-beamformers for giving a delay to each of the vibrators are mounted. When the 2D probe is used, ultrasonic signals of transmission and reception can be two-dimensionally controlled, and a three-dimensional image can be acquired. When a three-dimensional image can be acquired, calculation of the volume of an organ or the like, which is very complicated in the related art, becomes easy.

In the 2D probe, since the vibrators are arranged two-dimensionally, the number of the vibrators may exceed 10,000 channels. Further, it is necessary to mount the micro-beamformers individually on the vibrators. Along with this, the manufacturing process becomes complicated, and as a result, a short circuit failure easily occurs between adjacent channels in the manufacturing process. On the other hand, in the 2D probe, since signals are averaged for transmission and reception, even when a short circuit failure occurs in apart of the channels, the image is hardly affected.

However, when such a short circuit failure occurs, for example, when polarity of high voltage signals at the time of transmission is different between adjacent channels, a large current may flow through a short-circuited part. Accordingly, the reliability may decrease, and the power consumption may increase. That is, the 2D probe in which a short-circuit failure has occurred needs to be handled as a defective product even though there is no difference between the defective product and a non-defective product in the performance of an ultrasonic image.

It should be noted that, when the technology of PTL 1 is used, it is possible to determine whether the 2D probe is a non-defective product or a defective product, but it is difficult to reduce a product defect rate. In addition, in the technology of PTL 1, a dedicated test circuit including a high breakdown voltage transistor or the like is required, and in particular, there is a concern about an increase in the area overhead in a 2D probe having a large limitation on a circuit area.

The invention has been made in view of the above circumstances, and an object thereof is to provide an ultrasonic probe, an ultrasonic diagnostic device, and a manufacturing method of the ultrasonic probe, which are capable of reducing a product defect rate.

The object described above, other objects, and novel features of the invention will be clarified with the description of this specification and the accompanying drawings.

Solution to Problem

An outline of a representative embodiment of the inventions disclosed in the present application will be briefly described as follows.

An ultrasonic probe according to an embodiment includes a plurality of channels. Each of the plurality of channels includes a vibrator that is configured to output an ultrasonic wave, and a transmission circuit unit that is configured to change an output in response to an input transmission signal and cause the vibrator to output the ultrasonic wave by driving the vibrator with the output. Here, the transmission circuit unit includes a stop signal holding circuit that holds a stop signal when the stop signal is input in advance, and selects whether to change the output in response to the transmission signal based on whether the stop signal is held.

Advantageous Effect

To briefly describe the effects obtained according to the representative embodiment of the inventions disclosed in the present application, the product defect rate can be reduced.

BRIEF DESCRIPTION OF DRAWINGS

FIG. 1 is a schematic diagram illustrating an example of a configuration example of a main part and an example of a test method, of an ultrasonic probe according to a first embodiment of the invention.

FIG. 2 is a sequence graph illustrating an example of transmission signals transmitted to respective channels and an example of current change of an ammeter in FIG. 1.

FIG. 4 is a schematic diagram illustrating a configuration example of a main part of an ultrasonic probe corresponding to FIG. 3A.

FIG. 5 is a sequence graph illustrating an example of transmission signals transmitted to the respective channels and an example of current change of an ammeter in FIGS. 3B and 4.

FIG. 6 is a schematic diagram illustrating an example of an ultrasonic probe test method using the test pattern in FIG. 3B.

FIG. 7 is a flowchart illustrating an example of processing contents at the time when the test method of FIG. 6 is implemented with a test process in FIG. 24.

FIG. 8 is a sequence graph illustrating an example of measurement results of a power source current based on FIGS. 6 and 7.

FIG. 9 is diagram in which the measurement result in FIG. 8 is mapped.

FIG. 10 is a schematic diagram illustrating a configuration example of a control circuit in FIG. 1.

FIG. 11 is a circuit diagram illustrating a detailed configuration example of the control circuit in FIG. 10.

FIG. 12 is a sequence graph illustrating an operation example of the control circuit in FIG. 11.

FIG. 13 is a schematic diagram illustrating an example of a test method for an ultrasonic probe according to a second embodiment of the invention.

FIG. 14 is a sequence graph illustrating examples of current change of an ammeter in a case where the test method in FIG. 13 is used.

FIG. 15 is a flowchart illustrating an example of processing contents at the time when the test method of FIG. 13 is implemented with the test process in FIG. 24.

FIG. 16 is a schematic diagram illustrating an example of a test method in an ultrasonic probe according to a third embodiment of the invention.

FIG. 17 is a schematic diagram illustrating an example of a test method in a case where there is a short-circuited channel in FIG. 16.

FIG. 18 is a flowchart illustrating an example of processing contents at the time when the test methods of FIGS. 16 and 17 are implemented with the test process in FIG. 24.

FIG. 19 is a schematic diagram illustrating an example of a test method in an ultrasonic probe according to a fourth embodiment of the invention.

FIG. 20 is a schematic diagram illustrating an example of a test method in a case where there is a short-circuited channel in FIG. 19.

FIG. 21 is a schematic diagram illustrating an example of a test method in an ultrasonic probe according to a fifth embodiment of the invention.

FIG. 22 is a schematic diagram illustrating a configuration example of an ultrasonic diagnostic device according to the first embodiment of the invention.

FIG. 23 is a schematic diagram illustrating a configuration example of an ultrasonic probe in FIG. 22.

FIG. 24 is a flowchart illustrating an example of a main process in a manufacturing method of the ultrasonic probe according to the first embodiment of the invention.

DESCRIPTION OF EMBODIMENTS

Figure 3A:
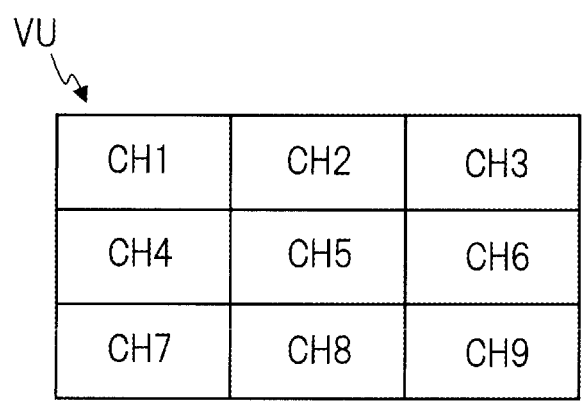
FIGS. 3A and 3B are schematic diagrams illustrating an arrangement configuration example of a plurality of channels, and an example of a test pattern thereof.

In the following embodiments, description may be divided into a plurality of sections or embodiments if necessary for convenience, unless particularly specified, these embodiments are not independent with each other, but in a relationship in which one embodiment is a variation, detailed description, supplementary description, or the like of a part or all of another embodiment. In the following embodiments, when numerical information and the like (including number of article, numerical value, quantity, range and the like) of an element are referred to, these parameters are not limited to specific numbers, and the values may be equal to or greater than or equal to or less than these specific numbers, unless particularly specified or unless otherwise apparently limited to specific numbers in principle.

Further, in the following embodiments, it is needless to say that the constituent elements (including element steps and the like) are not necessarily essential, unless particularly specified or considered to be apparently essential in principle. Similarly, in the following embodiments, when referring to shapes, positional relationships, and the like of the constituent elements and the like, substantially approximate or similar shapes and the like are included therein, unless particularly specified or considered to be apparently excluded in principle. The same also applies to the numerical values and the ranges described above.

Hereinafter, embodiments of the invention will be described in detail with reference to the drawings. In all the drawings for describing the embodiments, the same members are denoted by the same reference numerals in principle, and the repetitive description thereof will be omitted.

First Embodiment

<Schematic Configuration of Ultrasonic Diagnostic Device>

FIG. 22 is a schematic diagram illustrating a configuration example of an ultrasonic diagnostic device according to a first embodiment of the invention. An ultrasonic diagnostic device 100 of FIG. 22 includes an ultrasonic probe PB, an ultrasonic diagnostic device body 101 that is connected to the ultrasonic probe PB via a cable 105 and performs power source supply and control for the ultrasonic probe PB, and a display 102. The ultrasonic probe PB is, for example, a matrix probe (2D probe), and includes a vibrator module UM including both a transducer unit VU and a control Integrated Circuit (IC) 106 for controlling the transducer unit VU. The control IC 106 is configured with, for example, one semiconductor chip.

The ultrasonic diagnostic device body 101 includes a self-diagnosis unit 103, a power source circuit 104, and an image processing unit (not shown). The self-diagnosis unit 103 performs a test on the ultrasonic probe PB, which will be described in detail below. The power source circuit 104 generates a power source (for example, several volts to ±several tens of volts) of the control IC 106 disposed in the ultrasonic probe PB. The image processing unit performs image processing on a signal from the ultrasonic probe PB, and displays a processing result thereof on the display 102 or the like.

The ultrasonic diagnostic device body 101 includes, for example, a Central Processor Unit (CPU) that performs control over the entire device including the ultrasonic probe PB, a Digital Signal Processor (DSP), a storage device, a communication interface, and a user interface, as actual hardware. For example, the self-diagnosis unit 103 is implemented by program processing or the like using the CPU, and the image processing unit is implemented by the DSP or the like. The user interface is, for example, a keyboard, a mouse, or a touch panel on the display 102.

FIG. 23 is a schematic diagram illustrating a configuration example of the ultrasonic probe PB in FIG. 22. The ultrasonic probe PB includes a plurality of channels. Each of the plurality of channels includes a vibrator 2 that outputs an ultrasonic wave, and a channel control unit (micro-beamformer) 110 that controls the vibrator 2. Specifically, the ultrasonic probe PB includes a transducer unit VU and the control IC 106. In the transducer unit VU, vibrators 2 as many as the channels are formed. In the control IC 106, channel control units 110 as many as the channels are formed in a manner corresponding to the respective vibrators 2. Each channel is disposed two-dimensionally in a row direction (X) and a column direction (Y), and in this example, the channels are arranged in n rows and m columns.

Although illustration is omitted, the transducer unit VU is disposed, for example, in an upper part (in a height direction (Z)) of the control IC 106 in actual implementation. The vibrator 2 in the transducer unit VU and the channel control unit 110 in the control IC 106 are connected to each other by a wiring line LN in each channel. The channel control unit 110 includes a transmission circuit 1, a reception circuit 111, and a control circuit 9. The control circuit 9 outputs a transmission signal to the transmission circuit 1 in response to an instruction from the ultrasonic diagnostic device body 101, and outputs a reception signal from the reception circuit 111 to the ultrasonic diagnostic device body 101.

The transmission circuit 1 changes an output in response to a transmission signal input via the control circuit 9, and causes the vibrator 2 to output an ultrasonic wave by driving the vibrator 2 with the output. The reception circuit 111 receives a reflection waveform from a target via the vibrator 2, and outputs a reception signal to the control circuit 9. The control circuit 9 includes a variable delay circuit 91. The variable delay circuit 91 appropriately controls a delay time (phase) of the transmission signal to the transmission circuit 1 and a delay time (phase) of the reception signal from the reception circuit 111. At this time, by setting an appropriate delay time (phase) to each variable delay circuit 91 of the plurality of channels, it is possible to control a direction of the target in two dimensions.

The control IC 106 includes a row peripheral circuit 115, a column peripheral circuit 116, and a memory 120. The row peripheral circuit 115 controls the channel control units 110 on a row basis via n sets of row control signals 117. The column peripheral circuit 116 controls the channel control units 110 on a column basis via m sets of column control signals 118. Each of the control signals (117, 118) includes a selection signal for selecting a specific channel, a setting signal for setting a delay time of each channel, and the like. The memory 120 stores setting information 121 in which a channel to be stopped (a channel as an input target of a stop signal) is set, which will be described in detail below.

<Manufacturing Method of Ultrasonic Probe>

FIG. 24 is a flowchart illustrating an example of a main process in a manufacturing method of the ultrasonic probe according to the first embodiment of the invention. In FIG. 24, various manufacturing devices manufacture a transducer unit VU in which the vibrators 2 of the plurality of channels are formed (step S401).

Subsequently, the transducer unit VU and a previously manufactured control IC 106 are prepared, and a vibrator module UM is assembled by wiring the vibrator 2 and the channel control unit 110 for each of the plurality of channels (step S402). Next, the vibrator module UM and a cable are connected, and the ultrasonic probe PB is assembled (step S403). Further, an inspection device, which will be described in detail below, uses a transmission signal for test to test the ultrasonic probe PB so as to determine the setting information 121 shown in FIG. 23 (step S404).

In such a flow, for example, when the transducer unit VU is manufactured (step S401) or when the ultrasonic module UM is assembled (step S402), a short circuit failure may occur between adjacent channels. Particularly, in a 2D probe that includes over 10000 channels, since a large number of the channels are arranged at a high density, the probability that a short circuit failure occurs increases.

On the other hand, for example, even when a short circuit failure occurs in apart of the channels (for example, about several percent), it is possible to substantially acquire a diagnostic image of a level which is the same as one acquired in a case where there is no short circuit failure. However, when a short circuit failure occurs, the failure may spread in a wide range due to heat generation or the like, with this failure part as a starting point. In addition, problems such as an increase in power consumption and a power supply drop may occur. Therefore, the ultrasonic probe PB in which a short circuit failure has occurred is regarded as a defective product. At this time, since it is regarded as a defective product after an assembling process of step 403, a cost loss is increased. Therefore, it is beneficial to use a method of the embodiments described below.

<Configuration and Test Method of Ultrasonic Probe>

FIG. 1 is a schematic diagram illustrating an example of a configuration example of a main part and an example of a test method, of an ultrasonic probe according to a first embodiment of the invention. The ultrasonic probe includes a plurality of channels (three channels CH1 to CH3 for simplification of description), and each channel includes the vibrator 2 and a transmission circuit unit 8. The transmission circuit unit 8 includes the transmission circuit 1 and the control circuit 9 that are shown in FIG. 23, changes an output in response to an input transmission signal TX, and causes the vibrator 2 to output an ultrasonic wave by driving the vibrator 2 with the output.

The control circuit 9 transmits a transmission signal TX of an "H" level or an "L" level to the transmission circuit 1 in response to an instruction from the ultrasonic diagnostic device body 101 (see FIG. 22). The transmission circuit 1 includes a pre-driver 3 and a driver 4. As a circuit system of the transmission circuit 1 of an ultrasonic probe, a pulse circuit system that outputs discrete values of "H"/"L", a linear circuit system that outputs a continuous wave such as a sine wave, and the like are generally known. Here, a case where a pulse circuit system is used is described as an example, and alternatively other circuit systems may be used.

The pre-driver 3 changes an output of the driver 4 by driving the driver 4 in response to the transmission signal TX input via the control circuit 9. For example, when the transmission signal TX is at the "H" level, the output of the driver 4 is also the "H" level, and when the transmission signal TX is at the "L" level, the output of the driver 4 is also at the "L" level. The driver 4 causes the vibrator 2 to output an ultrasonic wave by driving the vibrator 2 with the changed output. The transmission signal TX (and the output of the driver 4) is not limited to two values of "H" level/"L" level, and alternatively may be three values of the "H" level (positive voltage level)/a 0 V level/the "L" level (negative voltage level).

Here, the driver 4 of each of the channels CH1 to CH3 is connected to a positive high-voltage power source 5 and to a negative high-voltage power source 7, which are common power sources. An ammeter 6 that measures a power source current is connected between the common power source (positive high-voltage power source 5 in this example) and the driver 4. At the time of testing the ultrasonic probe PB, the common power source and the ammeter 6 are mounted in the power source circuit 104 (see FIG. 22) of the ultrasonic diagnostic device body 101 or mounted in an inspection device.

That is, in the embodiment, after shipment of the ultrasonic probe PB, the ultrasonic probe PB can be tested via the cable 105 by using the self-diagnosis unit 103 (see FIG. 22) of the ultrasonic diagnostic device body 101. For example, the short circuit failure of the described above ultrasonic probe PB may occur or become obvious after shipment. The self-diagnosis unit 103 is provided such that the ultrasonic probe PB can be continuously used even in this case. In this case, the common power source and the ammeter 6 are mounted in the power source circuit 104 (see FIG. 22) of the ultrasonic diagnostic device body 101. Meanwhile, before shipment of the ultrasonic probe PB, as shown in step S404 of FIG. 24, the ultrasonic probe PB is tested by using an inspection device. In this case, the common power source and the ammeter 6 are mounted in the inspection device.

Here, in the example of FIG. 1, a short circuit failure occurs between a channel CH2 and a channel CH3. In this case, by using a transmission signal TX for test, for example, the output of the driver 4 of the channel CH2 is set to an "H" level, and an output of the channel CH3 is set to an "L" level. As a result, since a potential difference occurs between the outputs of the drivers 4, there is a current flowing from the channel CH2 to the channel CH3 via a short circuit resistor 10. By detecting this current with the ammeter 6, a short circuit failure between adjacent channels can be detected.

Meanwhile, the control circuit 9 holds operation availability information that is for selecting (presence/absence of output change) whether or not to change the output of the corresponding transmission circuit 1 in response to the transmission signal TX. The control circuit 9 holds operation availability information of the absence of the output change when a stop signal STP is input. Accordingly, in the example of FIG. 1, by inputting the stop signal STP to the control circuit 9 of the channels (referred to as short-circuited channel) CH2 and CH3 in which there is a short circuit failure, actual operations of the short-circuited channels CH2 and CH3 can be stopped. As a result, the ultrasonic probe PB in which a short circuit failure occurred may be handled as a non-defective product.

The control circuit 9 that holds the operation availability information of the absence of the output change, for example, fixes the output of the corresponding transmission circuit 1 to a 0 V level or the like. However, not particularly limited thereto, the control circuit 9 may perform control so as not to generate a potential difference between the outputs of the transmission circuits 1 of the short-circuited channels, for example, such that both the outputs of the transmission circuits 1 of the short-circuited channels are fixed to the "H" level or the "L" level. In some cases, the control circuit 9 may control the output of the transmission circuit 1 of the short-circuited channel to high impedance.

FIG. 2 is a sequence graph illustrating an example of transmission signals transmitted to respective channels and an example of current change of an ammeter in FIG. 1. As shown in FIG. 2, a short circuit current $I_{short}$ occurs when output logic of the short-circuited channel is inverted. Here, for simplification, a case where the channel CH2 is at the "H" level and the channel CH3 is at the "L" level is shown, but this case is the same as a case where the channel CH2 is at the "L" level and the channel CH3 is at the "H" level. That is, by performing control such that a potential difference occurs between the short-circuited channels, a short circuit failure can be detected. For example, in a three-value output pulse transmission circuit, a logic level of the transmission signal TX may be set such that a potential difference occurs between the short-circuited channels, and in a linear transmission circuit, a voltage level of the transmission signal may be adjusted such that a potential difference occurs between the short-circuited channels.

Further, by detecting the short circuit current $I_{short}$, it is possible to calculate a short-circuit resistance value in addition to detecting the presence or absence of a short circuit failure. Specifically, when an output voltage of an "H" level of the transmission circuit 1 is taken as "$V_{OH}$" and an output voltage of an "L" level is taken as "$V_{OL}$", a resistance value $R_{short}$ of the short circuit resistor 10 in FIG. 1 can be represented by Expression (1).

$$R_{short}=I_{short}/(V_{OH}-V_{OL}) \quad (1)$$

By calculating the resistance value $R_{short}$ of the short circuit resistor 10 in this manner, identification of a short circuit state is possible. For example, a very small resistance value is obtained when metals are short-circuited, and a relatively large resistance value is obtained when insulation resistance is reduced. Accordingly, for example, a resistance threshold, which causes problems to reliability, heat dissipation or the like, is set in advance, and it is possible to determine whether or not to stop the channel based on a comparison between the resistance threshold and the resistance value $R_{short}$ of Expression (1).

In the example of FIG. 1, the ammeter 6 is connected to the positive high-voltage power source 5, and detection is performed with an observation channel set to the "H" level and a short-circuited target channel set to "L" level. Alternatively, for example, the ammeter 6 may be connected to the negative high-voltage power source 7, and the detection may be performed with the observation channel set to the "L" level and the short-circuited target channel set to the "H" level. In the case of three-value output, the outputs of the transmission circuits 1 of the short-circuited channels may be set to the "H" level/0 V level or the "L" level/0 V level.

Figure 3B:
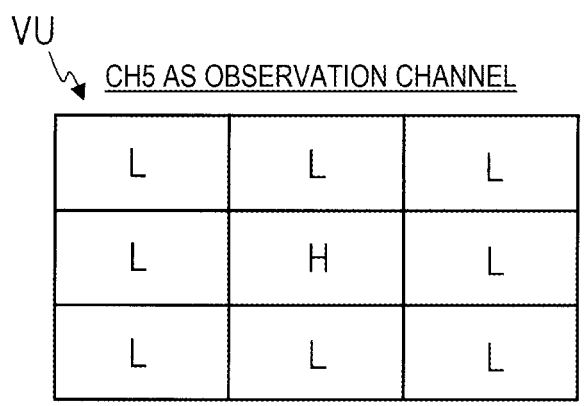

FIGS. 3(a) and 3(b) are schematic diagrams illustrating an arrangement configuration example of a plurality of channels, and an example of a test pattern thereof. FIG. 4 is a schematic diagram illustrating a configuration example of a main part of an ultrasonic probe corresponding to FIG. 3(a). FIG. 5 is a sequence graph illustrating an example of transmission signals transmitted to the respective channels and an example of current change of an ammeter in FIGS. 3(b) and 4. In FIG. 3(a), for simplification of description, nine channels CH1 to CH9 are arranged in three rows and three columns. As shown in FIG. 4, each of the channels CH1 to CH9 includes the vibrator 2 and the transmission circuit unit 8 that are similar to those in the case of FIG. 1. In FIG. 4, the ammeter 6 is connected to the positive high-voltage power source 5 as in the case of FIG. 1.

Here, for example, a case where a channel CH5 is set as an observation channel is assumed. In this case, for example, a test pattern as shown in FIG. 3(b) is set by using the transmission signals TX for test transmitted to the respective channels shown in FIG. 4. In FIG. 3(b), an output level of the transmission circuit 1 of the observation channel CH5 is set to the "H" level, and output levels of eight channels (adjacent channels) CH1 to CH4 and CH6 to CH9 arranged adjacent to the observation channel are all set to the "L" level.

Accordingly, it is possible to detect a short circuit failure between the observation channel CH5 and the adjacent channels CH1 to CH4 and CH6 to CH9, and it is possible to determine whether a short circuit failure occurs in the observation channel CH5. In a case where a short circuit failure occurs between the observation channel and an adjacent channel, as shown in FIG. 5, a short circuit current $I_{short}$ flows when only the transmission signal TX of the observation channel CH5 is at the "H" level, and no short circuit current $I_{short}$ flows when the transmission signal TX of the observation channel CH5 is at the same "L" level as those of the adjacent channels CH1 to CH4 and CH6 to CH9.

FIG. 6 is a schematic diagram illustrating an example of a test method of an ultrasonic probe using the test pattern shown in FIG. 3(b). FIG. 7 is a flowchart illustrating an example of processing contents at the time of implementing the test method of FIG. 6 in the test process (step S404) of FIG. 24. FIG. 6 illustrates an example in which channels are arranged in 8 (A to H) rows and 10 (1 to 10) columns. In FIG. 7, an inspection device generally uses the transmission signals TX for test to change respective output levels of the transmission circuit units 8 of a plurality of channels, and identifies a channel (that is, a channel to which a stop signal STP is to be input) in which a short circuit failure occurs by detecting change in a power source current flowing through the common power source. In other words, the inspection device sets setting information 121 (operation availability information for each of the plurality of channels) that is stored in the memory 120 in FIG. 23.

In FIG. 7, specifically, after selecting an observation channel first (step S101), the inspection device uses the transmission signal TX for test to set the output level of the observation channel to the "H" level and all the output levels of the other channels including the adjacent channel to the "L" level (step S102). Accordingly, a state, in which a potential difference in the output levels of the transmission circuits 1 is generated between the observation channel and the adjacent channel, is constructed. In this state, the inspection device measures a power source current of the common power source by using the ammeter 6 (step S103), and stores a measurement result thereof (step S104).

Subsequently, the inspection device determines presence or absence of an unmeasured observation channel (step S105), and when there is an unmeasured observation channel, changes the observation channel such that the unmeasured observation channel is selected and returns the process to processing of step S102 (step S106). Further, the inspection device repeats the processing of steps S102 to S104 until there is no unmeasured observation channel (steps S105 and S106). In the example of FIG. 6, the observation channel is moved in an order of column 1 row A, column 1 row B . . . column 1 row H, column 2 row A, column 2 row B . . . column 10 row 10. Here, as an example of a stage of the manufacturing process of the ultrasonic probe PB, the inspection device executes the flow of FIG. 7, and the self-diagnosis unit 103 of the ultrasonic diagnostic device body 101 executes the flow in FIG. 7 at a stage after the ultrasonic probe PB is connected to the ultrasonic diagnostic device body 101.

FIG. 8 is a sequence graph illustrating an example of a measurement result of the power source current based on FIGS. 6 and 7. FIG. 9 is a diagram in which the measurement result in FIG. 8 is mapped. For example, in FIG. 6, it is assumed that a channel of column 2 row C (C2) and a channel of column 3 row D (D3) are short-circuited, and a channel of column 7 row E (E7) and a channel of column 8 row E (E8) are short-circuited. In this case, as shown in FIG. 8, when these channels are taken as observation channels, a power source current measured by the ammeter 6 exceeds a predetermined current threshold Ith.

The current threshold Ith can be determined, for example, by converting a predetermined short circuit resistance threshold into a current based on Expression (1). The inspection device compares the measured power source current with the current threshold Ith for each observation channel, determines an observation channel (C2, D3, E7 and E8 in this example) with a power source current exceeding the current threshold Ith as a short-circuited channel, and as shown in FIG. 9, maps the short-circuited channel into a two-dimensional pattern. As a result, the inspection device (or a user thereof) can recognize that a short circuit occurs in the channels adjacent to each other, as indicated by reference numerals 20.

<Details of Control Circuit>

FIG. 10 is a schematic diagram illustrating a configuration example of the control circuit in FIG. 1. When a short-circuited channel is identified as illustrated in FIGS. 8 and 9, an operation of the short-circuited channel is stopped, and the ultrasonic probe PB including the short-circuited channel can be regarded as a non-defective product. At this time, more specifically, the inspection device, for example, determines whether the number of short-circuited channels with respect to a total number of channels is equal to or less than a predetermined ratio (for example, several percent), or whether an occurrence density of the short-circuited channels for each predetermined region is equal to or less than a predetermined density. The inspection device determines an ultrasonic probe PB as a non-defective product in a case where the number of the short-circuited channels is equal to or less than the predetermined ratio or in a case where the occurrence density of the short-circuited channels is equal to or less than the predetermined density, and determines the ultrasonic probe PB as a defective product in other cases. Hereinafter, a method of stopping the operation of the short-circuited channel in an ultrasonic probe PB that is determined as a non-defective product will be described.

The control circuit 9 shown in FIG. 10 includes a stop signal holding circuit 30 and an operation determination circuit 31. The stop signal holding circuit 30 holds a stop signal STP (in other words, operation availability information) when the stop signal STP is input in advance. The stop signal holding circuit 30 outputs the held stop signal STP to the operation determination circuit 31 in response to an enable signal EN. The enable signal EN is issued at a stage when input of the stop signals STP to all the short-circuited channels is completed. The operation determination circuit 31 selects whether or not to change the output in response to the transmission signals TX, based on the output from the stop signal holding circuit 30 (that is, based on presence and absence of held stop signal STP).

FIG. 11 is a circuit diagram illustrating a detailed configuration example of the control circuit of FIG. 10. FIG. 12 is a sequence graph illustrating an operation example of the control circuit of FIG. 11. As shown in FIG. 11, a row selection signal X_ON [n], a column selection signal Y_ON [m], and a transmission ON signal TX_ON are input into the stop signal holding circuit 30 as the stop signals STP. The row selection signal X_ON [n] and the column selection signal Y_ON [m] are input from the row peripheral circuit 115 and the column peripheral circuit 116 in FIG. 23, respectively. The transmission ON signal TX_ON is commonly input into all the channels.

The channel to which the stop signal STP is to be input is determined according to the row selection signal X_ON [n] and the column selection signal Y_ON [m]. That is, by setting one of n row selection signals and one of m column selection signals to the "H" level, one corresponding channel is selected. Here, in the selected channel, the "H" level is input into data input (D) of a flip-flop 43 via an AND operational circuit 41.

The column selection signal Y_ON [m] is input into another AND operational circuit 42, and an inverted signal of the transmission ON signal TX_ON is further input into the AND operational circuit 42. An output of the AND operational circuit 42 is at the "L" level when the transmission ON signal TX_ON is at the "H" level, and is at the "H" level when the transmission ON signal TX_ON is at the "L" level. Therefore, when the transmission ON signal TX_ON is changed from the "H" level to the "L" level, the output of the AND operational circuit 42 is shifted from the "L" level to the "H" level, which is a clock input (CK) of the flip-flop 43. The flip-flop 43 holds the data input (D) at a rising edge of the clock input (CK) and transmits the data input (D) to output (Q).

Actually, when the stop signal STP is held in the stop signal holding circuit 30 of the short-circuited channel, as shown in FIG. 12, n channels corresponding to the column selection signal Y_ON [m] are selected by first controlling one column selection signal Y_ON [m] to be at the "H" level. Further, by controlling a single or a plurality of row selection signals X_ON [n] to be at the "H" level, a single or a plurality of channels corresponding to the short-circuited channel are selected from the n channels. Further, by changing the transmission ON signal TX_ON from the "H" level to the "L" level in a selection period, the output (Q) of the flip-flop 43 of the short-circuited channel is set to the "H" level.

At this time, in a non-short-circuited channel among the n channels corresponding to the column selection signal Y_ON [m], the output (Q) of the flip-flop 43 is set to the "L" level since the row selection signal X_ON [n] is at the "L" level. In addition, in "(n−1)×m" channels corresponding to column selection signals other than the column selection signal Y_ON [m], the clock input (CK) to the flip-flop 43 is not performed since the column selection signal Y_ON [m] is at the "L" level. Therefore, by performing such processing while sequentially setting the column selection signal Y_ON [m] corresponding to a presence part of the short-circuited channel to the "H" level, it is possible to hold the stop signal STP only in the short-circuited channel.

In FIG. 11, the AND operational circuit 44 outputs an output of the flip-flop 43 to the operation determination circuit 31 when the enable signal EN is at the "H" level. The operation determination circuit 31, for example, outputs the "L" level regardless of the transmission signal TX when the output of the AND operational circuit 44, which is an AND operational circuit, is at the "H" level, and outputs the transmission signal TX when the output of the AND operational circuit 44 is at the "L" level. Accordingly, when the stop signal holding circuit 30 holds the stop signal STP (that is, when the output of the AND operational circuit 44 is of the "H" level), the output of the control circuit 9 can be fixed to the "L" level, and an operation of a channel can be stopped.

<Application Example of Ultrasonic Diagnostic Device>

An actual application example of the ultrasonic diagnostic device which includes the processing illustrated in FIGS. 11 and 12 will be described. First, in the test process (step S404) of FIG. 24, the inspection device identifies a short-circuited channel through the flow of FIG. 7, and writes information on the short-circuited channel (that is, the setting information 121 in FIG. 23) into the memory 120 of FIG. 23. The ultrasonic diagnostic device body 101, for example, supplies power to the ultrasonic probe PB when the ultrasonic probe PB is connected, and thereafter reads the setting information 121 from the memory 120 of the ultrasonic probe PB.

Here, when the information on the short-circuited channel (that is, the setting information 121 in FIG. 23) is written into the memory 120 of FIG. 23, for example, the following method may be used. That is, the information on the short-circuited channel may be written into a nonvolatile memory provided in the ultrasonic probe PB (not shown), and at the time of actual use, the ultrasonic diagnostic device body 101 may read the information on the short-circuited channel and write the information on the short-circuited channel into the memory 120 of the ultrasonic probe PB.

Further, based on the setting information 121 read from the memory 120, the ultrasonic diagnostic device body 101 issues an instruction to the ultrasonic probe PB. The instruction is for inputting a stop signal STP to a channel serving as an input target of the stop signal STP. Specifically, the ultrasonic diagnostic device body 101 outputs, for example, an address signal for identifying a channel to be an input target of a stop signal STP, a transmission on signal TX_ON, and an enable signal EN to the ultrasonic probe PB.

The transmission ON signal TX_ON and the enable signal EN are commonly transmitted to the control circuits 9 of all the channels. Meanwhile, the address signal is input into the row peripheral circuit 115 and the column peripheral circuit 116 of FIG. 23. In response, the row peripheral circuit 115 and the column peripheral circuit 116 assert a row selection signal X_ON [n] and a column selection signal Y_ON [m], which are corresponding to the address signal, to the "H" level, respectively. Accordingly, a sequence as shown in FIG. 12 is executed. After all the input of the stop signal STP is completed, the ultrasonic diagnostic device body 101 outputs the enable signal EN.

In a case where the self-diagnosis unit 103 of FIG. 22 is used, the self-diagnosis unit 103 executes the flow of FIG. 7 installed on a program in advance, for example, at the time of activation of the ultrasonic diagnostic device 100 or when instructed by a user. Further, when a channel serving as an input target of a stop signal STP is identified through the flow of FIG. 7, the self-diagnosis unit 103 issues an instruction to the ultrasonic probe PB. The instruction is for inputting the stop signal STP to the identified channel.

Here, in order to input the stop signal STP to the short-circuited channel, for example, a method of providing, in the control IC 106 in FIG. 22, wiring lines as many as the channels may be considered. However, it is difficult to provide such wiring lines, particularly in a 2D probe or the like having a large number of channels. Therefore, in the example of FIG. 11, in order to prevent such an increase in wiring line, the row selection signal X_ON [n] and the column selection signal Y_ON [m] are used. Wiring lines (for example, address wiring lines) of the row selection signal X_ON [n] and the column selection signal Y_ON [m] are originally provided to control each channel during normal operation. Therefore, two wiring lines corresponding to the transmission ON signal TX_ON and the enable signal EN may be added substantially to the control IC 106.

Main Effect of First Embodiment

As described above, by using the system of the first embodiment, even when there is a short-circuited channel, by detecting the short-circuited channel and stopping the operation thereof, an ultrasonic probe PB that is originally defective can be regarded as a non-defective product, so that a defective product rate can be reduced. Further, by providing the self-diagnosis unit 103 in the ultrasonic diagnostic device body 101, it is also possible to relieve product defect of the ultrasonic probe PB due to temporal degradation or the like. Although an application example to a 2D probe is illustrated here, it is needless to say that application to a 1D probe or the like is also possible.

Second Embodiment

<Test Method of Ultrasonic Probe>

In the first embodiment described above, a method of detecting a short circuit failure between adjacent channels based on mapping of the short-circuited channel is described. In the second embodiment, a method of directly detecting a short circuit failure will be described. FIG. 13 is a schematic diagram illustrating an example of the test method for an ultrasonic probe according to the second embodiment of the invention. In FIG. 13, channels CH1 to CH9 are arranged in three rows and three columns, and a channel CH5 among the channels CH1 to CH9 is an observation channel. Although the test method is executed by an inspection device or the self-diagnosis unit 103 in the same manner as in the first embodiment, here, a case where the test method is executed by the inspection device is taken as an example.

In "Step 0", the inspection device controls the observation channel CH5 to an "H" level and the other adjacent channels CH1 to CH4 and CH6 to CH9 to an "L" level. In this case, when a short circuit failure occurs between the observation channel as a reference and an adjacent channel, a short circuit current flows as described in the first embodiment. From this state, the inspection device changes the adjacent channels one by one from the "L" level to the "H" level. For example, in "Step 1", the channel CH8 is changed to the "H" level, and in "Step 2", the channel CH9 is changed to the "H" level. When the channel changed to the "H" level is a short-circuited channel, no short circuit current flows since logic of the channel is equal to logic of the observation channel. Therefore, it is possible to directly detect that a short circuit failure occurs between the observation channel and which adjacent channel.

FIG. 14 is a sequence graph illustrating examples of current change of an ammeter in a case where the test method of FIG. 13 is used. A case where a short circuit failure occurs between the observation channel CH5 and the adjacent channel CH9 is considered as case 1. In "Step 0", when the observation channel CH5 is at the "H" level and the adjacent channels CH1 to CH4 and CH6 to CH9 are at the "L" level, a short circuit current flows. Thereafter, in "Step 2", since logic of the observation channel CH5 and that of the adjacent channel CH9 are equal at a stage where the adjacent channel CH9 is changed from the "L" level to the "H" level, no short circuit current flows. As a result, the adjacent channel CH9 can be detected as a short-circuited channel.

A case where a short circuit failure occurs between the observation channel CH5 and the adjacent channel CH7 is considered as case 2. Similarly to case 1, in "Step 8", since the logic of the observation channel CH5 and that of the adjacent channel CH7 are equal at a stage where the adjacent channel CH7 is changed from the "L" level to the "H" level, no short circuit current flows. As a result, the adjacent channel CH7 can be detected as a short-circuited channel.

A case where short circuit failures occur at two parts, between the observation channel CH5 and the adjacent channel CH7, and between the observation channel CH5 and the adjacent channel CH9, is considered as case 3. In this case, in "Step 2", the short circuit current is not zero but at an intermediate level determined by a ratio of short circuit resistance. Further, in "Step 8", the short circuit current is zero. Thus, by detecting change in power source current during sequentially changing the logic of the adjacent channels until the short circuit current is zero, it is possible to identify the short-circuited channel even when there are a plurality of short-circuited channels with the observation channel as reference.

FIG. 15 is a flowchart illustrating an example of processing contents at the time when the test method in FIG. 13 is implemented in the test process (step S404) in FIG. 24. In short-circuited channel identifying processing in FIG. 15, the inspection device first sets an output level of the transmission circuit 1 of the observation channel to the "H" level, and sets output levels of the transmission circuits 1 of the other channels to the "L" level (step S201). Subsequently, the inspection device measures the power source current using the ammeter 6 (step S202).

Next, the inspection device selects one of the adjacent channels, changes an output level of the transmission circuit 1 thereof from the "L" level to the "H" level (step S203), and measures the power source current (step S204). Thereafter, the inspection device repeats the processing of steps S203 and S204 until there is no adjacent channel (step S205). Although an order in which the adjacent channels are changed from the "L" level to the "H" level is counterclockwise, it is needless to say that the invention is not limited thereto, and other orders may be used. In addition, regarding the short-circuited channel identified in this manner, operation stop processing is performed using the method described in the first embodiment.

Main Effect of Second Embodiment

As described above, in the method of the second embodiment, the inspection device (or the self-diagnosis unit 103) searches for the adjacent channel between which and the observation channel a short circuit failure occurs, while changing the adjacent channels, between which and the observation channel a potential difference is generated, one by one with the observation channel as reference. Accordingly, in addition to obtaining various effects similar to those of the first embodiment, it is possible to detect a short circuit failure between the observation channel and the adjacent channel without performing mapping. That is, for example, the power source current may exceed a current threshold due to a factor other than a short circuit failure between adjacent channels. In this case, the ultrasonic probe PB may not be regarded as a non-defective product. When the method of the second embodiment is used, differentiation thereof can be directly performed.

Third Embodiment

<Test Method of Ultrasonic Probe>

The short-circuited channel is detected by individually moving the observation channel in the first embodiment, and here another test method will be described. FIG. 16 is a schematic diagram illustrating an example of the test method for an ultrasonic probe according to the third embodiment of the invention. In FIG. 16, a case where a test is performed on channels of eight rows (A to H) and ten columns (1 to 10) is taken as an example. Although the test method is executed by an inspection device or the self-diagnosis unit 103 in the same manner as in the first embodiment, here, a case where the test method is executed by the inspection device is taken as an example.

In "Step 1", the inspection device, taking eight channels (rows A to H) of the same column as observation channels, measures a power source current in a state where output levels of the transmission circuits 1 thereof are controlled to be at an "H" level and all output levels of the other channels are controlled to be at an "L" level. Further, while the inspection device moves the observation channels column by column in units of the observation channels (that is, eight channels arranged in the same column), the inspection device controls output level of each channel to be the same, and measures the power source current each time the observation channels are moved.

When the last column (column 10) in column is reached, in "Step 2", the inspection device, taking ten channels (columns 1 to 10) of the same row as observation channels, measures the power source current in a state where output levels of the transmission circuits 1 thereof are controlled to be the "H" level and all output levels of the other channels are controlled to be the "L" level. Further, the inspection device moves the observation channels row by row in units of the observation channels (that is, ten channels arranged in the same row), while the inspection device controls output level of each channel to be the same, and measures the power source current each time the observation channels are moved.

Here, it is assumed that there is no short-circuited channel. In this case, when the observation channel is moved channel by channel as in the first embodiment, measurement of the power source current needs to be performed "8×10" times. On the other hand, as in the third embodiment, when the observation channel is moved in units of columns and rows, measurement of the power source current only needs to be performed "10+8" times. As a result, it is possible to shorten test time.

FIG. 17 is a schematic diagram illustrating an example of a test method in a case where there is a short-circuited channel in FIG. 16. In FIG. 17, a case where a channel of row F column 3 (F3) and a channel of row F column 4 (F4) are short-circuited channels will be described as an example. In "Step 1", when measurement of the power source current is performed while the observation channel is being moved in units of columns from the first column, a short circuit current flows when the observation channels are those in the third column (that is, when each channel in the third column is of the "H" level and the other channels are of the "L" level). Accordingly, it is determined that there is a short-circuited channel in the third column.

In this case, as shown in "Step 1-2", the inspection device measures the current current while changing the eight channels (rows A to H) present in the third column from the "H" level to the "L" level one by one. At this time, when the channel of row F is changed to the "L" level, no short circuit current flows. Accordingly, it is determined that the channel of "F3" is a short-circuited channel. Thereafter, in "Step 1-3", if the short-circuited channel identifying processing described in the second embodiment is performed using the channel of "F3" as the observation channel, it is determined that a short circuit failure occurs between the channel of "F3" and the channel of "F4".

FIG. 18 is a flowchart illustrating an example of processing contents at the time when the test methods of FIGS. 16 and 17 are implemented in the test process (step S404) in FIG. 24. In FIG. 18, the inspection device first selects a column to be set as an observation channel (step S301). Subsequently, the inspection device sets output levels of the transmission circuits 1 of the selected observation channel column to the "H" level and output levels of the other channels to the "L" level (step S302), and measures the power source current using the ammeter 6 in this state (step S303).

Next, the inspection device determines presence or absence of a short circuit failure based on a measurement result of the power source current (step S304). When there is no short circuit failure, the inspection device shifts the process to step S310, and when there is a short circuit failure, the inspection device shifts the process to step S305. The inspection device changes row n of a target column, in which a short circuit failure is detected, to the "L" level in step S305, and in this state, measures the current current in step S306. Here, when there is no change in the measurement result of the current current, the inspection device adds the row (n) to be changed to the "L" level (step S308), and repeats the processing of steps S305 and S306 (step S307).

On the other hand, when there is change in the measurement result of the current current in step S307, the inspection device executes the short-circuited channel identifying processing shown in FIG. 15, taking the row n of the target column as the observation channel (step S309). Thereafter, in step S310, the inspection device determines presence and absence of an unmeasured column, and when there is an unmeasured column, the inspection device repeats executing the processing of steps S301 to S309 while moving the column (step S311). On the other hand, when there is no unmeasured column in step S310, the inspection device executes processing similar to that in steps S301 to S310, taking a row as observation channel instead of a column (steps S401 to S410).

Here, although the test is performed first in units of columns, it is needless to say that the test may be performed first in units of rows. The specific method of the short-circuited channel identifying processing in steps S309 and S409 is not limited to that shown in FIG. 15, and alternatively other methods may be used. In addition, regarding the short-circuited channel identified in this manner, operation stop processing is performed using the method described in the first embodiment.

Main Effect of Third Embodiment

As described above, by using the method of the third embodiment, it is possible to obtain an effect of shortening the test time in addition to the various effects described in the first and second embodiments.

Fourth Embodiment

<Test Method of Ultrasonic Probe>

FIG. 19 is a schematic diagram illustrating an example of a test method for an ultrasonic probe according to a fourth embodiment of the invention. In FIG. 19, a case where a test is performed on channels of eight rows (A to H) and ten columns (1 to 10) is taken as an example. Although the test method is executed by an inspection device or the self-diagnosis unit 103 in a similar manner as in the first embodiment, here, a case where the test method is executed by the inspection device is taken as an example. As shown in FIG. 19, the inspection device measures a current current while controlling an output level of the transmission circuit 1, in units of a plurality of channels arranged in a staggered pattern.

Specifically, the inspection device divides all the channels into units UT, with four channels adjacent in a row direction and a column direction as one unit UT. Further, as illustrated in "Step 1", the inspection device, controls an output level of one specific channel in the unit UT to be an "H" level and all the other channels to be an "L" level, and measures the current current in a state where the entire channel is set in a test pattern of a staggered pattern. Thereafter, in "Step 2" to "Step 4", the inspection device measures the current current while changing clockwise the channel in the unit UT to be the one specific channel. Accordingly, when there is no short-circuited channel, the test can be completed by performing measurement of the current current four times.

FIG. 20 is a schematic diagram illustrating an example of the test method in a case where there is a short-circuited channel in FIG. 19. In the example of FIG. 20, a short circuit failure occurs between a channel of row D column 3 (D3) and a channel of row E column 2 (E2). In this case, at a stage of "Step 2" shown in FIG. 19, since the channel of "D3" is set to the "H" level and the channel of "E2" is set to the "L" level, a short circuit current flows.

In this case, as shown in "Step 2-1" in FIG. 20, the inspection device measures the power source current in a state where only one unit UT in the entire channel is set to a logic level of "Step 2". Further, the inspection device measures the current current while sequentially moving the single unit UT in a column direction (or a row direction). As a result, the inspection device detects a short circuit current when the current current is measured at a unit UT including the channel of "D3", and thus can identify the channel of "D3" as a short-circuited channel.

Thereafter, as shown in "Step 2-2", the inspection device can identify the channel of "E2" as another short-circuited channel by executing the short-circuited channel identifying processing of FIG. 15, taking the channel of "D3" as the observation channel. Regarding the short-circuited channel identified in this manner, operation stop processing is performed using the method described in the first embodiment.

Main Effect of Fourth Embodiment

As described above, by using the method of the fourth embodiment, it is possible to obtain an effect of shortening the test time in addition to the various effects described in the first and second embodiments.

Fifth Embodiment

<Test Method of Ultrasonic Probe>

FIG. 21 is a schematic diagram illustrating an example of a test method for an ultrasonic probe according to a fifth embodiment of the invention. In FIG. 21, a case where a test is performed on channels of eight rows (A to H) and ten columns (1 to 10) is taken as an example. Although the test method is executed by an inspection device or the self-diagnosis unit 103 in the same manner as in the first embodiment, here, a case where the test method is executed by the inspection device is taken as an example.

As shown in FIG. 21, in "Step 1-1", the inspection device measures a current current in a state where an output level of each channel located in an odd-numbered column is set to an "H" level and an output level of each channel located in an even-numbered column is set to an "L" level. Subsequently, in "Step 1-2", the inspection device measures the current current in a state where the output level of each channel located in the even-numbered column is set to the "H" level and the output level of each channel located in the odd-numbered column is set to the "L" level.

In "Step 2-2", the inspection device measures the current current in a state where the output level of each channel located in an even-numbered row is set to the "H" level and the output level of each channel located in an odd-numbered row is set to the "L" level. Subsequently, in "Step 2-2", the inspection device measures the current current in a state where the output level of each channel located in the even-numbered row is set to the "H" level and the output level of each channel located in the odd-numbered row is set to the "L" level.

Accordingly, when there is no short-circuited channel, the test can be completed by performing measurement of the current current four times. Here, when a short circuit current is detected, for example, it is possible to identify the short-circuited channel by using the same method as that in the case of FIG. 17. At this time, a short-circuited channel may be identified, with either the odd-numbered column (odd-numbered row) or even-numbered column (even-numbered row) as target. Regarding the short-circuited channel identified in this manner, operation stop processing is performed using the method described in the first embodiment.

Main Effect of Fifth Embodiment

As described above, by using the method of the fifth embodiment, it is possible to obtain an effect of shortening the test time in addition to the various effects described in the first and second embodiments.

While the invention made by the present inventors has been specifically described based on the embodiments, the invention is not limited to the embodiments described above, and various changes and modifications may be made without departing from the scope of the invention. For example, the embodiments described above have been described in detail for easy understanding of the invention, the invention is not necessarily limited to those including all the configurations described above. Apart of the configuration of one embodiment can be replaced with the configuration of another embodiment, and the configuration of another embodiment can be added to the configuration of one embodiment. A part of the configuration of each embodiment may be added, deleted, or replaced with another configuration.

For example, here, the ultrasonic diagnostic device body 101 reads the setting information 121 from the memory 120 of the ultrasonic probe PB, and issues an instruction to the ultrasonic probe PB based on the setting information 121. The instruction is for inputting a stop signal STP to a channel serving as an input target of the stop signal STP. However, in some cases, it is also possible that the ultrasonic probe PB itself reads the setting information 121 from the memory 120 and inputs the stop signal STP to the transmission circuit 1 of the ultrasonic probe PB based on the read setting information 121.

REFERENCE SIGN LIST 1 transmission circuit
2 vibrator
5 positive high-voltage power source
6 ammeter
7 negative high-voltage power source
8 transmission circuit unit
9 control circuit
30 stop signal holding circuit
101 ultrasonic diagnostic device
103 self-diagnosis unit
105 cable
106 control IC
120 memory 121 setting information
CH channel
LN wiring line
PB ultrasonic probe
STP stop signal
TX transmission signal
VU transducer unit

The invention claimed is:

1. A manufacturing method of an ultrasonic probe including a plurality of channels,
wherein the plurality of channels are two-dimensionally arranged in a row direction and a column direction,
each of the plurality of channels including
a vibrator that is configured to output an ultrasonic wave, and
a transmission circuit unit that is configured to hold operation availability information indicating whether or not to change an output in response to an input transmission signal, and, when to change the output based on the operation availability information, causes the vibrator to output the ultrasonic wave by driving the vibrator with the output, and
the transmission circuit units of the plurality of channels being connected to a common power source,
the manufacturing method comprising:
a first step of assembling the ultrasonic probe, by preparing a transducer unit in which the vibrators of the plurality of channels are formed and a control IC in which the transmission circuit units of the plurality of channels are formed, and by wiring the vibrator and the transmission circuit unit for each of the plurality of channels; and
a second step of determining the operation availability information for each of the plurality of channels, by an inspection device taking the ultrasonic probe as a target and detecting change in a power source current flowing through the common power supply while changing each output level of the transmission circuit units of the plurality of channels by using the transmission signal for test,
wherein in the second step, the inspection device compares the power source current with a predetermined current threshold, in a state where a potential difference is generated in the output levels of the transmission circuit units between an observation channel and an adjacent channel arranged adjacent to the observation channel, and
wherein in the second step, the inspection device searches for the adjacent channel, between which and the observation channel a short circuit failure occurs, while changing one by one the adjacent channel, between which and the observation channel a potential difference is generated, taking the observation channel as a reference.

2. The manufacturing method of the ultrasonic probe according to claim 1, wherein
in the second step, the inspection device controls the output level of the transmission circuit unit in units of the plurality of channels arranged in the same column, or in units of the plurality of channels arranged in the same row.

3. The manufacturing method of the ultrasonic probe according to claim 1, wherein
in the second step, the inspection device controls the output level of the transmission circuit unit in units of the plurality of channels arranged in a staggered pattern.

4. The manufacturing method of the ultrasonic probe according to claim 1, wherein
the ultrasonic probe further includes a memory that stores the operation availability information as setting information for each of the plurality of channels, and
in the second step, the inspection device writes the setting information into the memory.

* * * * *